(12) United States Patent
Dubnau et al.

(10) Patent No.: US 9,441,223 B2
(45) Date of Patent: Sep. 13, 2016

(54) TRANSPOSABLE ELEMENTS, TDP-43, AND NEURODEGENERATIVE DISORDERS

(71) Applicant: Cold Spring Harbor Laboratory, Cold Spring Harbor, NY (US)

(72) Inventors: Josh Dubnau, Huntington, NY (US); Wanhe Li, New York, NY (US); Lisa Prazak, Massapequa Park, NY (US); Molly Hammell, Cold Spring Harbor, NY (US); Ying Jin, Syosset, NY (US)

(73) Assignee: Cold Spring Harbor Laboratory, LLC, Cold Spring Harbor, NY (US)

( * ) Notice: Subject to any disclaimer, the term of this patent is extended or adjusted under 35 U.S.C. 154(b) by 44 days.

(21) Appl. No.: 14/019,380

(22) Filed: Sep. 5, 2013

(65) Prior Publication Data
US 2014/0113952 A1 Apr. 24, 2014

Related U.S. Application Data

(60) Provisional application No. 61/697,056, filed on Sep. 5, 2012.

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |
| C12Q 1/68 | (2006.01) |

(52) U.S. Cl.
CPC .......... *C12N 15/113* (2013.01); *C12Q 1/6883* (2013.01); *C12Q 2600/106* (2013.01); *C12Q 2600/158* (2013.01)

(58) Field of Classification Search
CPC ................ A61K 48/00; C12N 15/111
See application file for complete search history.

(56) References Cited

FOREIGN PATENT DOCUMENTS

WO  WO2013/012806  1/2013

OTHER PUBLICATIONS

Voigt et al. (PLoS One, Aug. 2010, vol. 5, Issue 8, pp. 1-12, e12247).*
Verma et al., "ALS syndrome in patients with HIV-1 infection," J. Neurol. Sci. vol. 240, p. 59-64, Oct. 19, 2005.
Douville et al., "Identification of Active Loci of a Human Endogenous Retrovirus in Neurons of Patients with Amyotrophic Lateral Sclerosis," Ann. Neurol. vol. 69(1)141-151, Jan. 2011.
Geser et al., "Amyotrophic lateral sclerosis, frontotemperal dementia and beyond: the TDP-43 diseases," J. Neurol. vol. 256, No. 8, p. 1205-1214 (1-16 for citations), 2009.
Baugh et al., "Chronic traumatic encephalopathy: neurodegeneration following repetitive concussive and subconcussive brain trauma," Bain Imaging Behav. vol. 6, No. 2, p. 244-254, Jun. 2012.
Ou et al., "Cloning and characterization of a novel cellular protein, TDP-43, that binds to Human Immunodeficiency Virus Type 1 TAR DNA sequence motifs," Journal of Virology, vol. 69, No. 6, p. 3584-3596, Jun. 1995.
Kato et al., "Segmental copy-number gain within the region of isopentenyl disphosphate isomerase genes in sporadic amyotrophic lateral sclerosis," Biochemical and Biophysical Research Communications, 402, 2010, pp. 438-442.
Monte et al., "Characterization of the AD7C-NTP cDNA Expression in Alzheimer's Disease and Measurement of a 41-kD Protein in Cerebrospinal Fluid," J. Clin. Invest. V. 100, No. 12, p. 3093-3104, Dec. 1997.
Xing et al., Mobile elements create structural variation: Analysis of a complete human genome, Genome Res. vol. 19, p. 1516-1526, May 13, 2009.
Hormozdiari et al., Next-generation VariationHunter: combinatorial algorithms for transposon insertion discovery, Bioinformatics, vol. 26, pp. i350-i357, Jun. 15, 2010.
International Search Report and Written Opinion issued in counterpart PCT Application No. PCT/US2013/058290.
Kaneko et al., "DICER1 deficit induces Alu RNA toxicity in age-related macular degeneration," Nature Mar. 17, 2011; 471(7338):325-330. doi:10.1038/nature09830.
Tan et al., "Retrotransposon activation contributes to fragile X premutation rCGG-mediated neurodegeneration," Human Molecular Genetics, 2012, vol. 21, No. 1, doi:10.1093/hmg/ddr437.
Belgnaoui et al., "Human LINE-1 Retrotransposon Induces DNA Damage and Apoptosis in Cancer Cells", Cancer Cell International, 2006, vol. 6, No. 11., pp. 1-10 (available from http://www.cancerci.com/content/6/1/13).
Gendron et al., "Rodent Models of TDP-43 Proteinopathy: Investigating the Mechanisms of TDP-43-Mediated Neurodegeneration", J Mol Neurosci, 2011, vol. 45. pp. 486-499.
Tollervey et al., "Characterizing the RNA Targets and Position-Dependent Splicing Regulation by TDP-43", Nature Neuroscience, 2011, vol. 14, No. 4, pp. 452-459.
Lathe et al., "Differential Display Detects Host Nucleic Acid Motifs Altered in Scrapie-Infected Brain", J. Mol. Biol., 2009, vol. 392, pp. 813-822.
Treangen et al., "Repetitive DNA and Next-Generation Sequencing: Computational Challenges and Solutions", Nature Reviews. Genetics, 2012, vol. 13, pp. 36-46.
Voigt et al., "TDP-43-Mediated Neuron Loss *In Vivo* Requires RNA-Binding Activity", Plos One, 2010, vol. 5, Issue 8, e12247.
Li et al., "Transposable Elements in TDP-43-Mediated Neurodegenerative Disorders", Plos One, 2012, vol. 7, Issue 9, e44099.
Extended European Search Report for Application No. 13835474.1; Dated May 11, 2016.

* cited by examiner

*Primary Examiner* — Amy Bowman
(74) *Attorney, Agent, or Firm* — McCarter & English, LLP

(57) ABSTRACT

A method that includes measuring the expression level of at least one transposon in a biological sample from a subject; and determining whether the measured transposon expression exceeds a predetermined level, and if so, administering to the subject a transposon inhibitor in an amount effective to reduce the expression level of a transposon.

19 Claims, 24 Drawing Sheets

TRANSPOSABLE ELEMENTS, TDP-43, AND NEURODEGENERATIVE DISORDERS

RELATED APPLICATIONS

The present application claims the benefit of U.S. Ser. No. 61/697,056, filed Sep. 5, 2012, the disclosure of which is hereby incorporated by reference in its entirety.

STATEMENT REGARDING FEDERALLY SPONSORED RESEARCH OR DEVELOPMENT

This invention was made with government support under NIH 2 P30 CA45508-24 and NIH 5R01-NS067690-05 awarded by the National Institutes of Health (NIH). The government has certain rights in the invention.

FIELD OF THE INVENTION

The present invention relates to neurodegenerative disorders and transposable elements (TEs), and in particular, methods for measuring TE expression levels; methods for treating, diagnosing, and assessing the risk of neurodegenerative disorders, particularly those associated with TAR DNA-binding protein 43 (TDP-43), including frontotemporal lobar degeneration (FTLD), amyotrophic lateral sclerosis (ALS), and Alzheimer disease (AD); methods for profiling TE expression in a biological sample; and methods for determining whether a disorder is associated with TDP-43.

BACKGROUND OF THE INVENTION

TAR DNA-binding protein 43 (TDP-43) is an hnRNP-like RNA binding protein implicated in a large number of cellular functions. These functions include repression of HIV transcription, regulation of alternative RNA splicing, control of mRNA stability, and mRNA biogenesis. See, e.g., Sephton et al, 2011, J. Biol. Chem. 286, 1204-1215; Tollervey et al., 2011, Nat. Neurosci. 14, 452-458; Polymenidou et al., 2011, Nat. Neurosci. 14, 459-468; Buratti et al., 2012, RNA Biol. 7, 420-429; Xiao et al, 2011, Mol. Cell. Neurosci. 47, 167-180.

TDP-43 is also implicated in pathological processes. Accumulation of TDP-43 containing cytoplasmic inclusions is a shared hallmark in a broad spectrum of neurodegenerative disorders, including amyotrophic lateral sclerosis (ALS), frontotemporal lobar degeneration (FTLD), and Alzheimer disease (AD). See, e.g., Cohen et al., 2011, Trends Mol. Med. 17, 659-667; Buratti et al., 2012, RNA Biol. 7, 420-429; Sendtner et al., 2011, Nat. Neurosci. 14, 403-405]. The mechanisms that link TDP-43 to neurodegeneration, however, are unclear, and there is a need for specific and improved methods for treating, profiling, and identifying neurodegenerative disorders associated with TDP-43.

The instant application meets these and other needs in the art, partly by developing and applying new methods to profile the transposable element (TE) transcriptome. These profiling studies unexpectedly show that TDP-43 broadly targets TEs, and that TEs are widely over-expressed in animal models of TDP-43-associated neurodegenerative disorders, as well as in patients with frontotemporal lobar degeneration (FTLD).

SUMMARY OF THE INVENTION

In its many embodiments, the present invention provides methods for measuring TE expression levels; for treating, diagnosing, and assessing the risk of neurodegenerative disorders, including those associated with TDP-43; for profiling TE expression in a biological sample; and for determining whether a disorder is associated with TDP-43. It further provides methods of assessing the risk of TDP-43 associated neurodegenerative disorder and diagnosing a TDP-43 associated neurodegenerative disorder.

Accordingly, in one embodiment, the invention provides a method comprising the steps of: (a) measuring the expression level of at least one transposon in a biological sample from a subject; and (b) determining whether the measured transposon expression exceeds a predetermined level, and if so, administering to the subject a transposon inhibitor in an amount effective to reduce the expression level of a transposon.

In one aspect, the method further comprises testing for the presence of a TDP-43 associated cytoplasmic inclusion in the subject. In another aspect, the subject is at risk of developing a TDP-43 associated neurodegenerative disorder, or alternatively, the subject has or is suspected of having a TDP-43 associated neurodegenerative disorder.

In another aspect, the neurodegenerative disorder can include frontotemporal lobar degeneration (FTLD), amyotrophic lateral sclerosis (ALS), Alzheimer disease (AD), corticobasal degeneration, chronic traumatic encephalopathy, a disorder associated with repetitive head injury, or a Lewy body disorder (such as Parkinson disease without or with dementia (PDD), and dementia with LBs (DLB) alone or in association with Alzheimer disease (AD)).

In another aspect, the transposon inhibitor is an inhibitor of a protein encoded by a transposon. More particularly, the protein encoded by the transposon is a transposase; an integrase; a reverse transcriptase; an endonuclease; a protein encoded by gag, pol, or env; an enzyme encoded by ORF1 of a non-LTR retrotransposon, or an enzyme encoded by ORF2 of a non-LTR retrotransposon. The transposon inhibitor may also be an anti-retroviral drug; an inhibitor of reverse transcription; an inhibitor of transposase or integrase activity; an inhibitor of endonuclease activity; a stimulator of DNA repair machinery; a zinc-finger that targets a transposon promoter region; a repressor that inhibits a transposon; an innate antiretroviral resistance factor; a small interfering RNAs (siRNA), short hairpin RNA (shRNA), morpholino, or antisense oligonucleotide directed to a TE transcript; an inhibitor that blocks intercellular transmission of transposon genetic material or protein; or an inhibitor of post-translational processing or proteolysis of a transposon-encoded protein.

In another aspect, the transposon in step (a) can be a DNA transposon or a retrotransposon, including an LTR retrotransposon or a non-LTR retrotransposon. The non-LTR transposon can include a LINE retrotransposon, such as L1, and the non-LTR transposon can include a SINE retrotransposon, such as an Alu sequence. In yet another aspect, the transposon in step (a) can be autonomous or non-autonomous.

In a second embodiment, the invention provides a method, comprising administering to a subject having or suspected of having a TDP-43 associated neurodegenerative disorder a transposon inhibitor in an amount effective to reduce the expression level of a transposon.

In one aspect, the method further comprises testing for the presence of a TDP-43 associated cytoplasmic inclusion in the subject. In another aspect, the method further comprises (a) measuring the expression level of at least one transposon in a biological sample from a subject; and (b) determining whether the measured transposon expression level in the subject exceeds a predetermined level.

In another aspect, the neurodegenerative disorder can include FTLD, ALS, AD, corticobasal degeneration, chronic traumatic encephalopathy, a disorder associated with repetitive head injury, or a Lewy body related disorder (such as Parkinson disease without or with dementia (PDD), and dementia with LBs (DLB) alone or in association with Alzheimer disease (AD)).

In another aspect, the transposon inhibitor is an inhibitor of a protein encoded by a transposon. More particularly, the protein encoded by the transposon is a transposase; an integrase; a reverse transcriptase; an endonuclease; a protein encoded by gag, pol, or env; an enzyme encoded by ORF1 of a non-LTR retrotransposon, or an enzyme encoded by ORF2 of a non-LTR retrotransposon. The transposon inhibitor may also be an anti-retroviral drug; an inhibitor of reverse transcription; an inhibitor of transposase or integrase activity; an inhibitor of endonuclease activity; a stimulator of DNA repair machinery; a zinc-finger that targets a transposon promoter region; a repressor that inhibits a transposon; an innate antiretroviral resistance factor; a small interfering RNAs (siRNA), short hairpin RNA (shRNA), morpholino, or antisense oligonucleotide directed to a TE transcript; an inhibitor that blocks intercellular transmission of transposon genetic material or protein; or an inhibitor of post-translational processing or proteolysis of a transposon-encoded protein.

In another aspect, the transposon can be a DNA transposon or a retrotransposon, including an LTR retrotransposon or a non-LTR retrotransposon. The non-LTR transposon can include a LINE retrotransposon, such as L1, and a SINE retrotransposon, such as an Alu sequence. In yet another aspect, the transposon can be autonomous or non-autonomous.

In a third embodiment, the invention provides a method, comprising administering to a subject having or suspected of having a neurodegenerative disorder (or at risk of developing a neurodegenerative disorder) a transposition inhibitor in an amount effective to reduce the expression level of a transposon, wherein the neurodegenerative disorder is selected from the group consisting of FTLD, ALS, AD, corticobasal degeneration, chronic traumatic encephalopathy, a disorder associated with repetitive head injury, and a Lewy body related disorder.

In one aspect, the transposon inhibitor is an inhibitor of a protein encoded by a transposon. More particularly, the protein encoded by the transposon is a transposase; an integrase; a reverse transcriptase; an endonuclease; a protein encoded by gag, pol, or env; an enzyme encoded by ORF1 of a non-LTR retrotransposon, or an enzyme encoded by ORF2 of a non-LTR retrotransposon. The transposon inhibitor may also be an anti-retroviral drug; an inhibitor of reverse transcription; an inhibitor of transposase or integrase activity; an inhibitor of endonuclease activity; a stimulator of DNA repair machinery; a zinc-finger that targets a transposon promoter region; a repressor that inhibits a transposon; an innate antiretroviral resistance factor; a small interfering RNAs (siRNA), short hairpin RNA (shRNA), morpholino, or antisense oligonucleotide directed to a TE transcript; an inhibitor that blocks intercellular transmission of transposon genetic material or protein; or an inhibitor of post-translational processing or proteolysis of a transposon-encoded protein.

In another aspect, the transposon can be a DNA transposon or a retrotransposon, including an LTR retrotransposon or a non-LTR retrotransposon. Non-LTR transposons can include a LINE retrotransposon, such as L1, and a SINE retrotransposon, such as an Alu sequence. In yet another aspect, the transposon can be autonomous or non-autonomous.

In a fourth embodiment, the invention provides methods for profiling TE expression in a biological sample. A first such method comprises (a) measuring the expression level of at least one transposon in a biological sample from the subject; and (b) determining whether the measured retrotransposon expression level in the biological sample exceeds a predetermined level. More particularly, the first method is MULTI mapping, as described herein. A second such method comprises (a) analyzing TEs that map uniquely to the genome; and (b) evaluating TEs that map to multiple locations, wherein the TEs map to the same element and wherein each TE location is weighted based on the number of alignments and is assigned an enrichment level. More particularly, the second method is UNIQ+SameEle mapping, as described herein.

For both sets of methods, the biological sample can be from a subject. Subjects include a transgenic animal, more particularly, a transgenic animal expressing a transgene encoding a protein involved in a neurological disorder. Subjects also include a human with a neurological disorder. More particularly, the neurological disorder is a neurodegenerative disorder, and even more particularly, is a TDP-43 associated neurodegenerative disorder.

For both sets of methods, TE expression can comprise expression of one or more of DNA transposons, LTR transposons, and non-LTR transposons, and more particularly, comprises expression of all three groups of transposons.

In a fifth embodiment, the invention provides a method of determining whether a disorder is associated with TDP-43, comprising (a) measuring the expression level of at least one transposon in a biological sample from a subject with the disorder; and (b) determining whether the measured transposon expression exceeds transposon expression levels in a control subject.

In one aspect, the method further comprises testing for the presence of a TDP-43 associated cytoplasmic inclusion in the subject. In another aspect the disorder is a neurological disorder, and more particularly, a neurodegenerative disorder.

In another aspect, the transposon can be a DNA transposon or a retrotransposon, including an LTR retrotransposon or a non-LTR retrotransposon. Non-LTR transposons can include a LINE retrotransposon, such as L1, and a SINE retrotransposon, such as an Alu sequence. In yet another aspect, the transposon can be autonomous or non-autonomous.

In a sixth embodiment, the invention provides a method of assessing whether a subject is at risk for developing a TDP-43 associated neurodegenerative disorder, the method comprising (a) measuring the expression level of at least one transposon in a test sample from a subject, and (b) comparing the measured level with a normal level, wherein a significant difference between the measured level and the normal level is an indication that the subject is at risk for developing a TDP-43 associated neurodegenerative disorder.

In a seventh embodiment, the invention provides a method of determining whether a subject is afflicted with a TDP-43 associated neurodegenerative disorder, the method comprising (a) measuring the expression level of at least one transposon in a test sample from a subject, and (b) comparing the measured level with a normal level, wherein a significant difference between the measured level and the normal level is an indication that the subject is afflicted with a TDP-43 associated neurodegenerative disorder.

In one aspect of the sixth or seventh embodiment, the method further comprises testing for the presence of a TDP-43 associated cytoplasmic inclusion in the subject. In another aspect, the neurodegenerative disorder is frontotemporal lobar degeneration (FTLD), amyotrophic lateral sclerosis (ALS), Alzheimer disease (AD), corticobasal degeneration, chronic traumatic encephalopathy, a disorder associated with repetitive head injury, or a Lewy body (LB) related disorder selected from the group consisting of Parkinson disease without or with dementia (PDD), and dementia with LBs (DLB) alone or in association with Alzheimer disease (AD).

In another aspect, the transposon can be a DNA transposon or a retrotransposon, including an LTR retrotransposon or a non-LTR retrotransposon. LTR transposons can include a LINE retrotransposon, such as L1, and a SINE retrotransposon, such as an Alu sequence. In yet another aspect, the transposon can be autonomous or non-autonomous.

In other embodiments, the transposon inhibitor is formulated as a composition or pharmaceutical composition, and can be administered in a therapeutically effective amount.

BRIEF DESCRIPTION OF FIGURES

For a more complete understanding of the invention, reference is now made to the Detailed Description and Examples in conjunction with the accompanying drawings.

DETAILED DESCRIPTION OF THE INVENTION

Figure 1A:
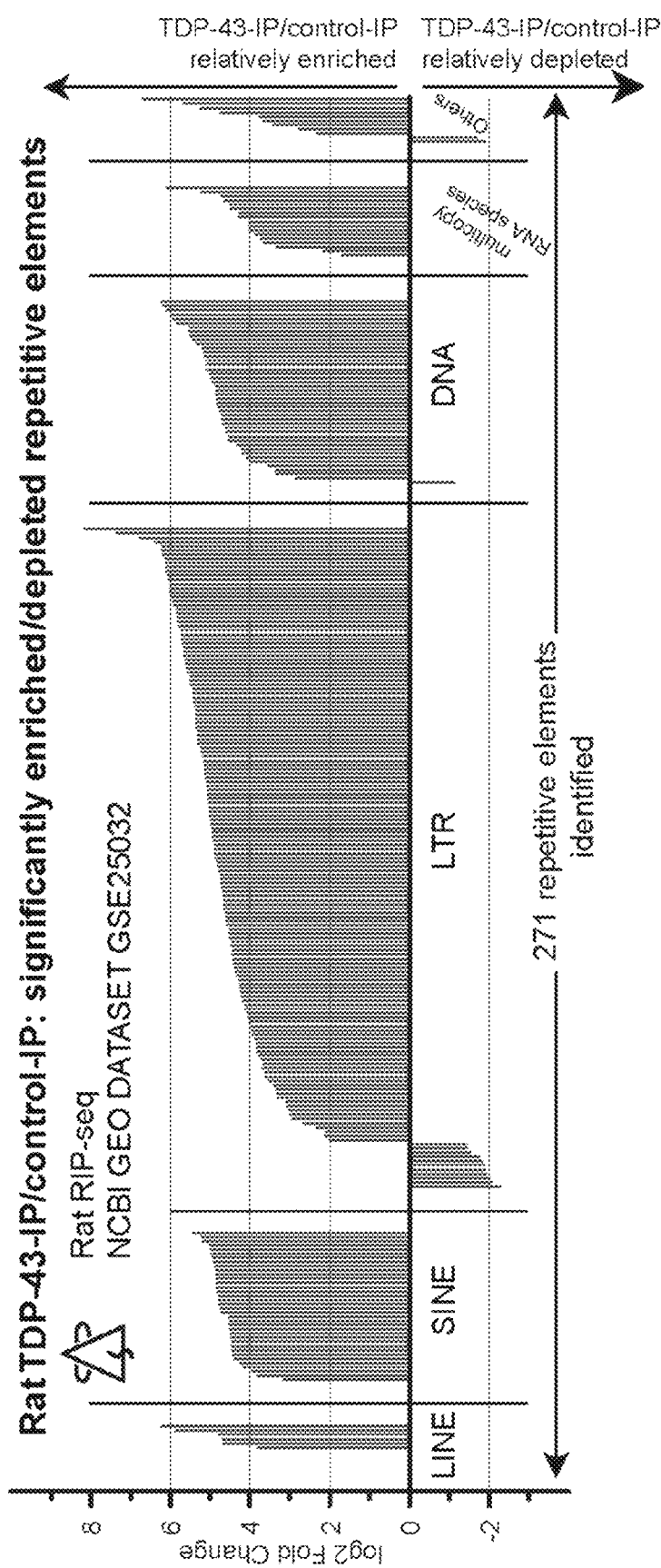
FIGS. 1A and 1B are histograms showing that TDP-43 binds broadly to TE-derived transcripts in rats (A) or mouse (B), each identified with the MULTI method. Shown are the magnitudes (log 2-fold) of enrichments (up) or depletions (down) for significantly bound repetitive elements grouped by class.

Unless otherwise defined, all technical and scientific terms used herein have the same meaning as commonly understood by one of ordinary skill in the pharmaceutical arts. Although methods and materials similar or equivalent to those described herein can be used in the practice or testing of the present invention, suitable methods and materials are described herein. All publications, patent applications, patents, and other references, including product descriptions, clinical studies, and protocols, mentioned in this application are incorporated by reference in their entirety. In addition, the materials, methods, and examples are illustrative only and are not intended to be limiting.

Reference is made to standard textbooks of molecular biology and pharmaceutics that contain definitions and methods and means for carrying out basic techniques, which may be encompassed by the present invention. See, e.g., Current Protocols in Pharmacology, Enna et al. (eds.), John Wiley and Sons, Inc., Hoboken, N.J. (2011), Current Protocols in Molecular Biology, Ausubel et al. (eds.), John Wiley & Sons, Inc., Hoboken, N.J. (2011), Current Protocols in Cell Biology, Bonifacino et al. (eds.), John Wiley & Sons, Inc.: Hoboken, N.J. (2011); Current Protocols in Neuroscience, Gerfen et al. (eds.), John Wiley & Sons, Inc., Hoboken, N.J. (2011); and the various references cited therein.

DEFINITIONS

The terms "comprising" and "including" are used herein in their open, non-limiting sense.

Other terms and phrases used in this document, and variations thereof, unless otherwise expressly stated, should be construed as open ended as opposed to limiting. As examples of the foregoing: the term "example" is used to provide exemplary instances of the item in discussion, not an exhaustive or limiting list thereof; adjectives such as "conventional," "traditional," "normal," "known," and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

As used herein, the terms "a," "an," and "the" are to be understood as meaning both singular and plural, unless explicitly stated otherwise. Thus, "a," "an," and "the" (and grammatical variations thereof where appropriate) refer to one or more.

As used herein, the term "about" or "approximately" means within an acceptable range for a particular value as determined by one skilled in the art, and may depend in part on how the value is measured or determined, e.g., the limitations of the measurement system or technique. As used herein, the term "about," when located before a dosage amount or dosage range of a specific ingredient, refers to an amount or range closely above or closely below the stated amount or range that does not manifestly alter the therapeutic effect of the specific ingredient from the stated amount or range and is meant to encompass at least all equivalents of that amount. For example, "about" can mean a range of up to 20%, up to 10%, up to 5%, or up to 1% or less of a given value. Alternatively, with respect to biological systems or processes, the term "about" can mean within an order of magnitude, within 5-fold, or within 2-fold of a value. Numerical quantities given herein are approximate unless stated otherwise, meaning that the term "about" or "approximately" can be inferred when not expressly stated.

A group of items linked with the conjunction "and" is not to be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances is not to be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

As used herein, the term "animal" or "subject" may be a vertebrate, in particular, a mammal, and more particularly, a human. A subject can also include a laboratory animal in the context of a clinical trial or screening or activity experiment. Thus, as can be readily appreciated by one of ordinary skill in the art, the compositions and methods of the present invention are particularly suited to administration to any vertebrate, particularly a mammal, and more particularly, a human.

As used herein, a "control subject" or a "normal subject" is an animal that is of the same species as, and otherwise comparable to (e.g., similar age, sex), the animal that is being tested, e.g., a test subject with a neurodegenerative disorder being measured for the expression level of at least one transposon in a biological sample from the test subject.

The terms "inhibit," "down-regulate," or "reduce" include decreasing expression of a gene, or level of RNA molecules or equivalent RNA molecules encoding one or more proteins or protein subunits, or activity of one or more gene products, proteins or protein subunits below that observed in the absence of one or more inhibitors, i.e., one or more transposon inhibitors, as defined herein.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients.

As used herein, the phrase "pharmaceutically acceptable" refers to molecular entities and compositions that are generally regarded as "safe," e.g., that are physiologically tolerable and do not typically produce an allergic or similar untoward reaction, such as gastric upset, dizziness and the like, or other significant adverse events, when administered to a human. Preferably, as used herein, the term "pharmaceutically acceptable" means approved by a regulatory agency of the Federal or a state government of listed in the U.S. Pharmacopeia or other generally recognized pharmacopeia for use in animals, and more particularly in humans.

In particular, the term "pharmaceutically acceptable salts" refers to salts prepared from pharmaceutically acceptable non-toxic bases or acids including inorganic bases or acids and organic bases or acids. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, and diethanolamine salts. See Stahl and Wermuth (eds), Pharmaceutical Salts; Properties, Selection, and Use: 2nd Revised Edition, Wiley-VCS, Zurich, Switzerland (2011).

The term "carrier" refers to an adjuvant, vehicle, or excipient, with which the compound is administered. In preferred embodiments of this invention, the carrier is a solid carrier. Suitable pharmaceutical carriers include those described in Remington: The Science and Practice of Pharmacy, 21st Ed., Lippincott Williams & Wilkins (2005).

The term "dosage form," as used herein, is the form in which the dose is to be administered to the subject or patient. The drug or supplement is generally administered as part of a formulation that includes nonmedical agents. The dosage form has unique physical and pharmaceutical characteristics. Dosage forms, for example, may be solid, liquid or gaseous. "Dosage forms," may include for example, a capsule, tablet, caplet, gel caplet (gel cap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the terms "inactive" and "inert" refer to any compound that is an inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

The terms "pharmaceutical agent," "compound," or "drug" may be used interchangeably herein, and include pharmacologically active substances in isolated form, or mixtures thereof. For example, a pharmaceutical agent, compound or drug may be an isolated and structurally-defined product, an isolated product of unknown structure, a mixture of several known and characterized products, or an undefined composition comprising one or more products. Examples of such undefined compositions include for instance tissue samples, biological fluids, cell supernatants, vegetal preparations, etc. The pharmaceutical agent, compound or drug may be any organic or inorganic product, including a polypeptide (or a protein or peptide), a nucleic acid, a lipid, a polysaccharide, a chemical entity, or mixture or derivatives thereof. The pharmaceutical agent, compound or drug may be of natural or synthetic origin, and the compound(s) or modulators may include libraries of compounds.

A pharmaceutical agent can decrease the amount, degree, or nature of transposon expression in vivo, in vitro, or ex vivo, relative to the amount, degree, or nature of transposon expression in the absence of the agent or reagent. In certain embodiments, treatment with such a pharmaceutical agent, such as a transposon inhibitor, may decrease the amount, degree, or nature of transposon expression by at least about 1%, 2%, 3%, 4%, 5%, 10%, 20%, 40%, 50%, 75%, 100%, 200% (2 fold), 300% (3 fold), 400% (4 fold), 500% (5 fold), or still more or less, compared to the amount, degree, or nature of transposon expression in the absence of the agent, under the conditions of the method used to detect or determine transposon expression.

Formulations

Compounds in accordance with the present invention can be administered alone, or alternatively, in the form of pharmaceutical composition. The compounds (as well as compositions and processes) of the present invention may also be used in the manufacture of a medicament for the therapeutic applications described herein Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a transposase inhibitor as an active ingredient (or a pharmaceutically acceptable salt thereof), and may also contain a pharmaceutically acceptable carrier and optionally other therapeutic ingredients.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. A compound (transposon inhibitor) of the present invention is typically formulated into pharmaceutical dosage forms to provide an easily controllable and appropriate dosage of the drug.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with any of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of transposon inhibitors can be determined by numerous means known in the art, such as comparing their in vitro activity, and in vivo activity in animal models. Methods for the extrapolation of effective dosages in mice, and other animals, to humans are known to the art.

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range of from about 0.01 to about 100 mg/kg, more specifically from about 0.1 to about 100/mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in unit dosage form; for example, containing 1 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

As used in the present disclosure, the term "therapeutically effective amount" means an amount or dose of a transposase inhibitor that is effective to ameliorate, delay, minimize, or prevent any symptom, behavior, or other event associated with a neurological disorder, disease, or condition, or any other nervous system disorder, disease, or condition specified herein. In a specific aspect, a therapeutically effective amount is the amount of a transposon inhibitor that is effective to reduce the expression level of a transposon, as disclosed herein.

Methods

Transposons

Transposons (or transposable elements (TEs)) are mobile genetic units that constitute a large fraction of most eukaryotic genomes. The movement and accumulation of TEs represent a major force in shaping the genes and genomes of almost all organisms. See, e.g., Feschotte and Pritham, 2007, Annu. Rev. Genet. 41, 331-368; Hancks and Kazazian, 2012, Curr. Opin. Gen. Dev. 22, 191-202; Burns and Boeke, 2012, Cell 149, 740-752; Lander et al., 2001, Nature 409, 860-921; Hua-Van et al, 2011, Biol. Dir. 6, 19.

Although many TE copies are nonfunctional, a subset has retained the ability to mobilize, and even immobile copies can be expressed. Moreover, several recent studies demonstrate that LINE-1 elements are normally active and mobile during neurogenesis in both rodent and human tissue. See, e.g., Coufal et al., 2009, Nature 460, 1127-1131; Muotri et al., 2005, Nature 435, 903-910. Some TEs appear to be normally active in the brain. For example, somatic mobilization of Alu and SVA elements as well as LINEs also has recently been detected in several different human brain regions. See, e.g., Baillie et al., 2011, Nature 479, 534-537; Muotri et al., 2005, Nature 435, 903-910; Muotri et al., 2009, Hippocampus 19, 1002-1007. Specific TEs have also been correlated with several neurodegenerative disorders. See, e.g., Greenwood et al., 2011, Mol. Neurodegener. 6, 44; Muotri et al., 2010, Nature 468: 443-446; Douville et al., 2011, Ann. Neurol. 69, 141-151; Lathe and Harris, 2009, J. Mol. Bio. 392, 813-822; Kaneko et al., 2011, Nature 471, 325-330; Tan et al., 2012, Human Mol. Genet. 21, 57-65; Jeong et al., 2010, J. Clin. Virol. 47, 136-142.

Because of their potential to copy themselves and insert into new genomic locations as well as to generate enormous levels of expression, transposable elements present a massive endogenous reservoir of genomic instability and cellular toxicity. See, e.g., Hua-Van et al., 2011, Biol. Dir. 6, 19. The impact of these parasitic genetic elements normally are stifled by potent cellular mechanisms involving small interfering RNAs that act via the RNA induced silencing complex (RISC) to inhibit transposon expression. For a review, see Saito et al, 2011, Dev. Cell 19, 687-697. Although most investigations have naturally focused on the germline, where new insertions are heritable and thus favored by transposon evolution, somatic tissues also have an active transposon silencing mechanism whose functional significance is less understood.

Transposable elements (TEs), or transposons, can be divided into three groups, or classes, based on their overall organization and mechanism of transposition. See, e.g., Ch. 11, Molecular Biology of the Gene, Watson J. D., et al., $6^{th}$ ed., CSHL Press, NY 2008. These groups comprise; (1) DNA transposons (also referred to as DNA elements, or DNA mobile elements); (2) Long terminal repeat (LTR) retrotransposons (also referred to as LTR transposons, LTR elements, and virus-like (retro) transposons); and (3) non-LTR retrotransposons (also referred to as non-viral (retro) transposons, or poly(A) retrotransposons). Collectively, LTR elements and non-LTR elements comprise retroelements, which are able to amplify to new locations in the genome through an RNA intermediate. Retroelements represent approximately 40% of the human genome, while DNA transposons account for about 2-3%. See, e.g., Lander et al., 2001, Nature 409, 860-921; Hua-Van et al., 2011, Biol. Dir. 6, 19. These three groups will now be described in more detail.

DNA Transposons

DNA transposons have sequences that function as recombination sites. These sites are at the two ends of the DNA element, are organized as inverted-repeat sequences, and carry the recognition sequences for recombination. DNA transposons can also carry genes encoding proteins responsible for transposition (usually called transposases, or sometimes, integrases). DNA transposons can exist as both autonomous elements (carrying a pair of inverted terminal repeats and a transposases gene), which have everything needed to promote their own transposition; and nonautonomous elements (carrying only the inverted terminal repeats), which depend on a "helper" transposon to donate the transposases needed for transposition.

DNA elements can move by non-replicative and replicative mechanisms. The non-replicative recombination pathway is called cut-and-paste transposition, because it involves excision of the transposon from its initial location in the host DNA, followed by integration of the excised transposon into a new DNA site. The replicative recombination pathway involves the duplication of the element DNA during each round of transposition.

LTR Retrotransposons

LTR retrotransposons, which include retroviruses, make up a significant fraction of the typical mammalian genome, comprising about 8% of the human genome and 10% of the mouse genome. Lander et al., 2001, Nature 409, 860-921; Waterson et al., 2002, Nature 420, 520-562. LTR elements include retrotransposons, endogenous retroviruses (ERVs), and repeat elements with HERV origins, such as SINE-R. LTR retrotransposons include two LTR sequences that flank a region encoding two enzymes: integrase and reverse transcriptase (RT).

ERVs include human endogenous retroviruses (HERVs), the remnants of ancient germ-cell infections. While most HERV proviruses have undergone extensive deletions and mutations, some have retained ORFS coding for functional proteins, including the glycosylated env protein. The env gene confers the potential for LTR elements to spread between cells and individuals. Indeed, all three open reading frames (pol, gag, and env) have been identified in humans, and evidence suggests that ERVs are active in the germline. See, e.g., Wang et al., 2010, Genome Res. 20, 19-27. Moreover, a few families, including the HERV-K (HML-2)

group, have been shown to form viral particles, and an apparently intact provirus has recently been discovered in a small fraction of the human population. See, e.g., Bannert and Kurth, 2006, Proc. Natl. Acad. USA 101, 14572-14579.

LTR retrotransposons insert into new sites in the genome using the same steps of DNA cleavage and DNA strand-transfer observed in DNA transposons. In contrast to DNA transposons, however, recombination of LTR retrotransposons involves an RNA intermediate. LTR retrotransposons make up about 8% of the human genome. See, e.g., Lander et al., 2001, Nature 409, 860-921; Hua-Van et al., 2011, Biol. Dir. 6, 19.

Non-LTR Retrotransposons

A non-LTR element terminates in 5' and 3' untranslated region (UTR) sequences and encodes two enzymes: ORF1, an RNA-binding enzyme; and ORF2, an enzyme having both reverse transcriptase and endonuclease activities Like LTR retrotransposons, non-LTR retrotransposons also move via an RNA intermediate. But the mechanism for mobilization of non-LTR retrotransposons—which is target-site primed reverse transcription (or "reverse splicing")—is different from the mechanism used for transposition by LTR retroelements.

Non-LTR retrotransposons include nonautonomous elements, such as Alu elements and SVA (SINE-VNTR-Alu) elements. Non-LTR transposons also include autonomous elements, such as LINEs ("long interspersed nuclear elements"). LINEs are abundant in the vertebrate genome, comprising about 20% of the human genome.

A well-studied LINE in humans is L1, which so far appears to be the only active autonomous retrotransposon in the human genome. However, LINEs such as L1 can donate the proteins necessary to reverse-transcribe and integrate another related class of repetitive sequences: the nonautonomous poly(A) retrotransposons known as SINEs ("short interspersed nuclear elements"). Genome sequences reveal the presence of huge numbers of SINEs, which are typically between 100 and 400 bp in length. The Alu sequence is an example of a widespread SINE in the human genome. The nonautonomous Alu elements, as well as processed pseudogenes, are retrotransposed in trans by the L1 retrotransposition proteins. Indeed, greater than 30% of the human genome has been generated through retrotransposition of LINE elements and other RNA species by the LINE reverse transcriptase. Cordaux and Batzer, 2009, Nat. Rev. Genet. 10, 691-703. Retrotransposition is ongoing in human populations as indicated by de novo L1, Alu, and SVA insertions associated with disease and by the large number of polymorphic insertions, many of which are at a low allele frequency in human genomes. See, e.g., Pickeral et al., 2000, Genome Res. 21, 985-990; Beck et al., 2010, Cell 141, 1159-1170; Huang et al., 2010, Cell 141, 1171-1182; Hormozdiari et al., 2011, Genome Res. 21, 840-849.

Treatments

Methods of the present invention include the use of a transposon inhibitor to treat disorders in a subject. As used herein, the term "disorder" may be used interchangeably with "condition" or "disease".

As used herein, the terms "treat," "treatment," "treating" include:
(i) prophylactic treatment, which includes preventing and/or reducing the incidence of and/or ameliorating the effect and/or duration of a disease, disorder, or condition from occurring in subjects that may get, be exposed to and/or be predisposed to the disease, disorder or condition, but may not yet have been diagnosed as having it; or are diagnosed as having the disease, disease, or condition; or are at risk of developing such disease, disorder, or condition;
(ii) inhibiting the disease, disorder, or condition, i.e., delaying the onset of a disease, disorder, or condition; arresting further development or progression of a disease, disorder, or condition in a subject already suffering from or having one or more symptoms of the disease, disorder, or condition; or reducing the risk of a disease, disorder, or condition worsening;
(iii) relieving the disease, disorder, or condition, i.e., causing regression of the disease, disorder, or condition, or one or more of its symptoms.

Disorders

In one aspect, the disorder in a neurological disease or disorder, particularly a neurodegenerative disorder. In another aspect, the neurodegenerative disorder is a TDP-43 associated neurodegenerative disorder. Neurodegenerative disorders within the scope of this invention include frontotemporal lobar degeneration (FTLD), amyotrophic lateral sclerosis (ALS), Alzheimer disease (AD), corticobasal degeneration, chronic traumatic encephalopathy, a disorder associated with repetitive head injury, or a Lewy body disorder (such as Parkinson disease without or with dementia (PDD), and dementia with LBs (DLB) alone or in association with Alzheimer disease (AD)).

Transposon Inhibitors

Transposon inhibitors include an inhibitor of a protein encoded by a transposon. More particularly, the protein encoded by the transposon can be a transposase; an integrase; a reverse transcriptase; an endonuclease; a protein encoded by gag, pol, or env; an enzyme encoded by ORF1 of a non-LTR retrotransposon, or an enzyme encoded by ORF2 of a non-LTR transposon.

Transposon inhibitors also include, but are not limited to, anti-retroviral drugs (such as AZT, abacavir, etravirine, or raltegravir); compounds that decrease TE RNA stability; inhibitor of reverse transcription, including nucleoside analog inhibitors (NRTIs) such as ddI, ddC, and stavudine, nucleotide analog inhibitors (NtRTIs) such as tenofovir and adeforvir, and non-nucleoside inhibitors (NNRTIs) such as nevirapine and efavirenz; inhibitors of transposase or integrase activity, inhibitors of endonuclease activity, and stimulators of DNA repair machinery, such as doxorubicin and phleomycin.

Furthermore, a transposon inhibitor can include: a zinc-finger protein ("zinc finger") that targets a transposon promoter region; a repressor that inhibits a transposon; an innate antiretroviral resistance factor, such as cAPOBEC3A or APOBEC3B, two members of the APOBEC3 family in humans—which can enter the nucleus and specifically inhibit both LINE-1 and Alu retrotransposition (see, e.g., Bogerd et al., 2006, Proc. Natl. Acad. Sci. USA 103, 8780-8785). Transposon inhibitors can also include small interfering RNAs (siRNAs), short hairpin RNA (shRNAs), morpholinos, and antisense oligonucleotides directed to TE transcripts; and inhibitors of post-translational processing or proteolysis of a transposon-encoded protein, such as the Env protein encoded by some LTR retrotransposons. They also include enzymes or repressors that inhibit TEs, for example, an enzyme that inhibits L1 (such as the protein APOBEC3G) or a repressor that inhibits L1 (such as MePC2 or Sox2).

Transposon inhibitors also include compounds that block transmission of a retroviral particles. For example, they may block binding of env-containing transposon particles to the corresponding receptor for the Env protein.

More generally, transposon inhibitors include compounds that prevent the spread of TEs between cells, i.e., that block intercellular transmission of transposon genetic material or protein. For example, inhibitors may be directed to the formation, transport, and movement of transposon RNAs in exosomes. Exosomes are formed by inward budding of late endosomes, producing multivesicular bodies (MVBs), and are released into the environment by fusion of the MVBs with the plasma membranes. Moreover, exosomes released from cells can contain messenger RNA (mRNA) and micro-RNA (miRNA) and can shuttle such RNAs and proteins from one cell to another. Exosomes can therefore be transported between different cells and influence physiological pathways in the recipient cells. See, e.g., Bang and Thum, 2012, Int. J. Biochem. Cell Biol. 10, 2060-2064.

TDP-43

TAR-DNA binding protein-43 (TDP-43) is an RNA binding protein containing two RNA-recognition motifs (RRM), a nuclear localization signal (NLS), a nuclear export signal (NES), as well as a C-terminal glycine-rich domain (GRD) implicated in TDP-43 protein interactions and functions. The protein is normally concentrated in the nucleus but also shuttles back and forth between the nucleus and cytoplasm.

TDP-43 aggregation and neuropathology plays a fundamental role in a broad spectrum of neurodegenerative disorders. See, e.g., Cohen et al., 2011, Trends Mol. Med. 17, 659-667; Buratti et al., 2012, RNA Biol. 7, 420-429; Sendtner et al., 2011, Nat. Neurosci. 14, 403-405]. Cytosolic accumulation of truncated TDP-43 is found in affected neurons of patients suffering from sporadic and familial ALS and FTLD. Cohen et al., 2011, Trends Mol. Med. 17, 659-667; Lander et al., 2001, Nature 409, 860-921; Hua-Van et al., 2011, Biol. Dir. 6, 19. Missense mutations clustering in the TDP-43 GRD have been identified in cases of ALS (and FTLD). See, e.g., Hancks and Kazazian, 2012, 22, 191-202; Saito and Siomi, 2010, Dev. Cell. 19, 687-697.

Elevated levels of the TDP-43 protein have also been identified in individuals diagnosed with chronic traumatic encephalopathy, a condition that often mimics ALS and that has been associated with athletes who have experienced multiple concussions and other types of head injury. See, e.g., Baugh et al, 2012, Brain Imaging Behav. 6, 244-254. TDP-43 pathology has also been implicated in tauopathies other than AD, such as corticobasal degeneration, as well as in Lewy body related disorders, including Parkinson's disease (PD) without or with dementia (PDD), and dementia with LBs (DLB) alone or in association with Alzheimer disease (AD). See, e.g., Uryu et al., 2008, J. Neuropathol. Exp. Neurol. 67, 555-564; Nakashima-Yasuda et al., 2007, Acta. Neuropathol. 114, 221-229.

TDP-43 was originally identified as a transcriptional repressor that binds to chromosomally integrated TAR DNA and represses HIV-1 transcription. Ou et al., 1995, J. Virol. 69, 3584-3596. TDP-43 is now implicated in many aspects of gene expression. Sendtner et al., 2011, Nat. Neurosci. 14, 403-405; Xiao et al., 2011, Mol. Cell. Neurosci. 47, 167-180. These observations have suggested that a central role of TDP-43 s to regulate alternative splicing of mRNA targets with a preference for those with large UG rich introns. See, e.g., Sephton et al., 2011, J. Biol. Chem. 286, 1204-1215; Tollervey et al., 2011, Nat. Neurosci. 14, 452-458; Polymenidou et al., 2011, Nat. Neurosci. 14, 459-468; Buratti et al., 2012, RNA Biol. 7, 420-429; Xiao et al., 2011, Mol. Cell. Neurosci. 47, 167-180.

As disclosed herein, however, TDP-43 also targets the mobile element derived transcriptome, i.e., transposable elements. Moreover, this association is defective in FTLD patients, and the TE transcriptome is broadly over-expressed in mouse models of TDP-43 pathology. (See Examples).

Accordingly, in one embodiment, the invention provides a method comprising the steps of: (a) measuring the expression level of at least one transposon in a biological sample from a subject; and (b) determining whether the measured transposon expression exceeds a predetermined level, and if so, administering to the subject a transposon inhibitor, as defined herein, in an amount effective to reduce the expression level of a transposon.

In one aspect, the method further comprises testing for the presence of a TDP-43 associated cytoplasmic inclusion in the subject. In another aspect, the subject is at risk of developing a TDP-43 associated neurodegenerative disorder, or alternatively, the subject has or is suspected of having a TDP-43 associated neurodegenerative disorder.

In another aspect, the neurodegenerative disorder can include frontotemporal lobar degeneration (FTLD), amyotrophic lateral sclerosis (ALS), Alzheimer disease (AD), corticobasal degeneration, chronic traumatic encephalopathy, a disorder associated with repetitive head injury, or a Lewy body disorder (such as Parkinson disease without or with dementia (PDD), and dementia with LBs (DLB) alone or in association with Alzheimer disease (AD)).

In another aspect, the transposon in step (a) can be a DNA transposon or a retrotransposon, including an LTR retrotransposon or a non-LTR retrotransposon. The LTR transposon can include a LINE retrotransposon, such as L1, and the non-LTR transposon can include a SINE retrotransposon, such as an Alu sequence. In yet another aspect, the transposon in step (a) can be autonomous or non-autonomous.

In a second embodiment, the invention provides a method, comprising administering to a subject having or suspected of having a TDP-43 associated neurodegenerative disorder a transposon inhibitor, as defined herein, in an amount effective to reduce the expression level of a transposon.

In one aspect, the method further comprises testing for the presence of a TDP-43 associated cytoplasmic inclusion in the subject. In another aspect, the method further comprises (a) measuring the expression level of at least one transposon in a biological sample from a subject; and (b) determining whether the measured transposon expression level in the subject exceeds a predetermined level.

In another aspect, the neurodegenerative disorder can include FTLD, ALS, AD, corticobasal degeneration, chronic traumatic encephalopathy, a disorder associated with repetitive head injury, or a Lewy body related disorder (such as Parkinson disease without or with dementia (PDD), and dementia with LBs (DLB) alone or in association with Alzheimer disease (AD)).

In a third embodiment, the invention provides a method, comprising administering to a subject having or suspected of having a neurodegenerative disorder (or at risk of developing a neurodegenerative disorder) a transposition inhibitor, as defined herein, in an amount effective to reduce the expression level of a transposon, wherein the neurodegenerative disorder is selected from the group consisting of FTLD, ALS, AD, corticobasal degeneration, chronic traumatic encephalopathy, a disorder associated with repetitive head injury, and a Lewy body related disorder.

In these methods, the transposon can be a DNA transposon or a retrotransposon, including an LTR retrotransposon or a non-LTR retrotransposon. The LTR transposon can include a LINE retrotransposon, such as L1, and the non-LTR transposon can include a SINE retrotransposon, such as an Alu sequence. In yet another aspect, the transposon can be autonomous or non-autonomous.

In certain embodiments, the transposon inhibitor is formulated as a composition or pharmaceutical composition, and can be administered in a therapeutically effective amount.

Assessing Risk of a TDP-43 Associated Disorder

In other embodiments, the invention provides a method of assessing whether a subject is at risk for developing a TDP-43 associated neurodegenerative disorder, the method comprising (a) measuring the expression level of at least one transposon in a test sample from a subject, and (b) comparing the measured level with a normal level, wherein a significant difference between the measured level and the normal level is an indication that the subject is at risk for developing a TDP-43 associated neurodegenerative disorder.

In one aspect, the method further comprises testing for the presence of a TDP-43 associated cytoplasmic inclusion in the subject. In another aspect, the neurodegenerative disorder is frontotemporal lobar degeneration (FTLD), amyotrophic lateral sclerosis (ALS), Alzheimer disease (AD), corticobasal degeneration, chronic traumatic encephalopathy, a disorder associated with repetitive head injury, or a Lewy body (LB) related disorder selected from the group consisting of Parkinson disease without or with dementia (PDD), and dementia with LBs (DLB) alone or in association with Alzheimer disease (AD).

In another aspect, the transposon can be a DNA transposon or a retrotransposon, including an LTR retrotransposon or a non-LTR retrotransposon. LTR transposons can include a LINE retrotransposon, such as L1, and non-LTR transposons can include a SINE retrotransposon, such as an Alu sequence. In yet another aspect, the transposon can be autonomous or non-autonomous.

Diagnosing a TDP-43 Associated Disorder

In other embodiments, the invention provides a method of determining, i.e, diagnosing, whether a subject is afflicted with a TDP-43 associated neurodegenerative disorder, the method comprising (a) measuring the expression level of at least one transposon in a test sample from a subject, and (b) comparing the measured level with a normal level, wherein a significant difference between the measured level and the normal level is an indication that the subject is afflicted with a TDP-43 associated neurodegenerative disorder.

In one aspect, the method further comprises testing for the presence of a TDP-43 associated cytoplasmic inclusion in the subject. In another aspect, the neurodegenerative disorder is frontotemporal lobar degeneration (FTLD), amyotrophic lateral sclerosis (ALS), Alzheimer disease (AD), corticobasal degeneration, chronic traumatic encephalopathy, a disorder associated with repetitive head injury, or a Lewy body (LB) related disorder selected from the group consisting of Parkinson disease without or with dementia (PDD), and dementia with LBs (DLB) alone or in association with Alzheimer disease (AD).

In another aspect, the transposon can be a DNA transposon or a retrotransposon, including an LTR retrotransposon or a non-LTR retrotransposon. LTR transposons can include a LINE retrotransposon, such as L1, and non-LTR transposons can include a SINE retrotransposon, such as an Alu sequence. In yet another aspect, the transposon can be autonomous or non-autonomous.

TE Profiling

The invention provides methods for profiling TE expression in a biological sample. A first such method comprises (a) measuring the expression level of at least one transposon in a biological sample from the subject; and (b) determining whether the measured retrotransposon expression level in the biological sample exceeds a predetermined level. More particularly, the first method is MULTI mapping analysis, as described herein.

A second such method comprises (a) analyzing TEs that map uniquely to the genome; and (b) evaluating TEs that map to multiple locations, wherein the TEs map to the same element and wherein each TE location is weighted based on the number of alignments and is assigned an enrichment level. More particularly, the second method is UNIQ+ SameEle mapping, as described herein.

For both sets of methods, the biological sample can be from a subject. Subjects include a transgenic animal, more particularly, a transgenic animal expressing a transgene encoding a protein involved in a neurological disorder. Subjects also include a human with a neurological disorder. The neurological disorder is a neurodegenerative disorder, and more particularly, is a TDP-43 associated neurodegenerative disorder.

For both sets of methods, TE expression can comprise expression of one or more of DNA transposons, LTR transposons, and non-LTR transposons, and more particularly, comprises all three groups of transposons.

Identifying TDP-43 Associated Disorders

The invention provides a method of determining whether a disorder is associated with TDP-43, comprising (a) measuring the expression level of at least one transposon in a biological sample from a subject with the disorder; and (b) determining whether the measured transposon expression exceeds transposon expression levels in a control subject.

In one aspect, the method further comprises testing for the presence of a TDP-43 associated cytoplasmic inclusion in the subject. In another aspect the disorder is a neurological disorder, and more particularly, a neurodegenerative disorder.

In another aspect, the transposon can be a DNA transposon or a retrotransposon, including an LTR retrotransposon or a non-LTR retrotransposon. The LTR transposon can includes a LINE retrotransposon, such as L1, and the non-LTR transposon can includes a SINE retrotransposon, such as an Alu sequence. In yet another aspect, the transposon can be autonomous or non-autonomous.

EXAMPLES

The present disclosure will be further illustrated by the following non-limiting Examples. These Examples are understood to be exemplary only, and they are not to be construed as limiting the scope of the invention as defined by the appended claims.

Example 1

TDP-43 Binds Broadly to TE-Derived Transcripts

Several recent studies have relied on deep sequencing to profile the RNA targets that co-purify with immunoprecipitated mouse, rat or human TDP-43 and also to profile gene expression changes in mouse after knockdown or over-expression of TDP-43. See, e.g., Sephton et al, 2011, J. Biol. Chem. 286, 1204-1215; Tollervey et al., 2011, Nat. Neurosci. 14, 452-458; Polymenidou et al., 2011, Nat. Neurosci. 14, 459-468; Shan et al., 2010, Proc. Natl. Acad. Sci. USA 107, 16325-16330; Buratti et al., 2012, RNA Biol. 7, 420-429; Sendtner et al., 2011, Nat. Neurosci. 14, 403-405. In each case, however, these studies analyzed annotated protein coding sequences and excluded TE-derived transcripts and other repetitive elements due to the difficulties inherent in working with ambiguously mapped reads from short read technologies. See, e.g., Treangen et al., 2012, Nat. Rev. Genet. 13, 36-46.

Despite efforts to develop new algorithms for analyzing multiple alignments of short reads (see e.g., Ji et al., 2011, Biometrics 67, 1217-1224), these algorithms have not been applied systematically for analyzing TE-derived transcripts in any neurodegenerative disease.

Because each of the above mentioned TDP-43 related studies provided public access to their raw data, this resource was used to search for TDP-43 targets and for transcript mis-expression when sequence reads that map to multiple genomic locations were included, the majority of which are TE derived transcripts in these datasets. As discussed below, by mining a series of deep sequencing datasets of protein-RNA interactions and of gene expression profiles, the following was uncovered: extensive binding of TE transcripts to TDP-43, an RNA-binding protein central to amyotrophic lateral sclerosis (ALS) and frontotemporal lobar degeneration (FTLD).

Methods

Data Preparation.

The CLIP-seq data of human healthy and FTLD brain tissues was obtained from EMBL-EBL Array Express Archive EMTAB-530. Tollervey et al., 2011, Nat. Neurosci. 14, 452-458. The RIP-seq data of rat cortical neuron cells was obtained from NCBI GEO DATASET GSE25032. Sephton et al, 2011, J. Biol. Chem. 286, 1204-1215. The mouse CLIP-seq and mRNA-seq datasets were obtained from NCBI GEO DATASET GSE22351 and GSE27394 (Polymenidou et al., 2011, Nat. Neurosci. 14, 459-468; Shan et al., 2010, Proc. Natl. Acad. Sci. USA 107, 16325-16330). The FUS PAR-CLIP-seq dataset (Da Cruz and Cleveland, 2011, Curr. Opin. Neurobiol. 21, 904-919) was downloaded from DDBJ Sequence Read Archive (DRA) SRA025082. The genome sequences (build rn4, hg19, and mm9), Ref-Gene annotations, and coordinates of repetitive elements in the whole genome of rat and human were downloaded from the University of California, Santa Cruz (UCSC) Genome Browser (Fujita et al., 2011, Nucl. Acids. Res. 39, D876-D882). Annotation strategies for identified peaks are described in more detail below.

Alignment.

Bowtie version 0.12.7 was used to align the short sequences. Langmead et al., 2009, Genome. Biol. 10, R25. Rat and human genome sequences were downloaded from the University of California, Santa Crutz (UCSC) Genome Browser (Fujita et al., 2011, Nucl. Acids. Res. 39, D876-D882). Two mismatches in the first 25 bp were allowed and the best alignments were reported. For non-uniquely mapped reads, allowing all possible alignments resulted in some reads that could potentially map to more than 10,000 regions. To capture the reads mapped to repetitive regions as much as possible while reducing the space and computational (time) cost, the -m option (reported number of alignments per sequence) was set to a value such that at least 90% of the reads with multiple alignments were reported. Specifically, -m 100, -m 500 and -m 200 were used on rat, mouse and human samples, respectively (command line e.g., -n 2-125-a -m 100 --best --strata). Each alignment was then assigned a weight such that the total weight of all reported alignments of each mapped read is the same. For example, if a read x uniquely maps to a region, then the weight of this alignment is 1. If a read y maps to two regions with the same quality, then each alignment y1 and y2 has weight 0.5, such that the total weight of y is 1. These weights were uniform among the alignments, and did not include a contribution from mapping quality scores because only equivalently mapped alignments were reported (i.e., the "--best --strata" options in the above command line). Table 1 summarizes the mapping results.

TABLE 1

Number of Aligned Reads for each TDP-43 Dataset

| | Reads after removing adapters | Uniquely mapped | Unique + multiple alignment |
|---|---|---|---|
| Human | | | |
| Healthy_brain_C23 | 1,821,484 | 29.64% | 41.34% |
| Healthy_brain_C25 | 3315218 | 62.08% | 87.31% |
| Healthy_brain_C30 | 2,214,683 | 40.59% | 74.99% |
| FTLD_TDP_brain_F20 | 2,368,609 | 22.56% | 87.85% |
| FTLD_TDP_brain_F21 | 1,565,761 | 40.76% | 85.92% |
| FTLD_TDP_brain_F24 | 1,699,368 | 20.06% | 82.42% |
| Rat | | | |
| Control | 25,626,886 | 15.41% | 84.32% |
| TDP-43 | 27,291,055 | 42.32% | 82.54% |
| Mouse | | | |
| CLIP-seq (Low Mnase) | 11,422,886 | 46.13% | 74.23% |
| RNA-seq control (rep 1.1) 61 | 16,280,064 | 63.77% | 82.2% |
| RNA-seq control (rep1.2) 66 | 21,522,132 | 64.35% | 81.46% |
| RNA-seq control (rep2.1) 62 | 17,874,867 | 62.95% | 82.81% |
| RNA-seq control (rep2.2) 67 | 23,654,429 | 64.39% | 82.6% |
| RNA-seq control (rep2.3) 68 | 23,872,449 | 64.42% | 82.67% |
| RNA-seq control (rep3.1) 63 | 15,384,509 | 62.99% | 83.29% |
| RNA-seq control (rep3.2) 69 | 20,366,829 | 64.87% | 83.32% |
| RNA-seq control (rep3.3) 70 | 20,051,210 | 63.88% | 83.25% |
| RNA-seq control (rep4.1) 64 | 17,026,225 | 64.74% | 83% |
| RNA-seq control (rep4.2) 65 | 16,800,571 | 63.45% | 82.5% |
| RNA-seq control (rep4.3) 71 | 23,401,256 | 62.59% | 82.49% |
| RNA-seq TDP43 (rep 1.1) 72 | 13,701,340 | 63.72% | 84.87% |
| RNA-seq TDP43 (rep 1.2) 73 | 13,098,290 | 62.22% | 82.69% |
| RNA-seq TDP43 (rep 1.3) 76 | 19,583,200 | 64.19% | 82.59% |
| RNA-seq TDP43 (rep 2.1) 74 | 17,330,196 | 63.42% | 84.79% |
| RNA-seq TDP43 (rep 2.2) 75 | 15,709,107 | 64.15% | 83.73% |
| RNA-seq TDP43 (rep 2.3) 77 | 19,346,369 | 63.35% | 81.35% |
| RNA-seq TDP43 (rep 3.1) 78 | 16,524,706 | 64.17% | 81.7&  |
| RNA-seq TDP43 (rep 3.2) 80 | 23,408,974 | 63.83% | 83.37% |

TABLE 1-continued

Number of Aligned Reads for each TDP-43 Dataset

|  | Reads after removing adapters | Uniquely mapped | Unique + multiple alignment |
|---|---|---|---|
| RNA-seq TDP43 (rep 4.1) 79 | 17,291,842 | 64.12% | 83.31% |
| RNA-seq TDP43 (rep 4.2) 81 | 23,333,313 | 64.34% | 83.34% |

The FUS dataset had shorter read lengths (36 nt) and lower sequencing quality than the TDP-43 datasets. For this dataset, reads at least 18 nt in length, after removing adapters and trimming the last few bases that have low qualities, were used. As summarized in Table 2, about 25% of the remaining reads from the FUS dataset mapped uniquely.

TABLE 2

Number of aligned reads for FUS datasets

| FUS | Reads after removing adapters and trimming | Uniquely mapped |
|---|---|---|
| Stable | 9,922,520 | 24.24% |
| Inducible 1 | 8,537,179 | 26.56% |
| Inducible 2 | 3,463,758 | 27.26% |
| R521G | 13,325,493 | 23.13% |
| R521H | 11,022,216 | 21.92% |

Finally, prior to normalization and peak identification, presumptive PCR duplicates were removed. For the human CLIP-seq datasets, where randomized nucleotides were included in the sample barcodes, PCR duplicates were identified directly and removed. For all other datasets, PCR duplicates were identified using the Picard "mark duplicates" task and removed prior to further analysis. While the reads in these samples were strand specific, the reads were allowed to map both sense and anti-sense to the Refseq and UCSC annotated gene and TE transcripts. While 98.5% of the reads that derive from Refseq transcripts mapped in the same orientation as the annotated gene, surprisingly, only 50% of the TE-mapped reads mapped to the annotated strand of the TE locus. This was true for both uniquely mapped reads as well as reads mapped to multiple loci.

Normalization.

Figure 4:
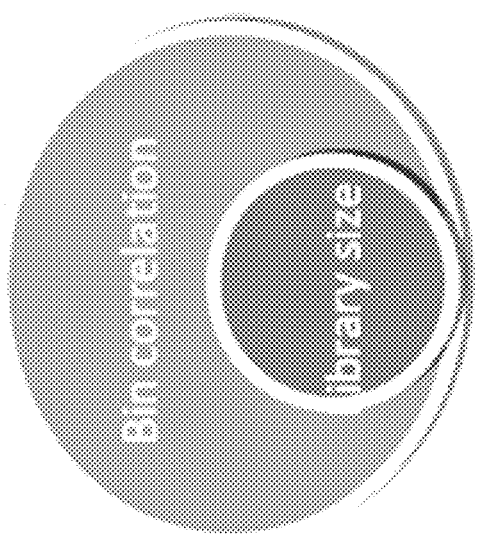
FIG. 4 is a pair of Venn diagrams showing the overlap of either total enriched TE peaks (left) or total depleted TE peaks (right) in rat TDP-43-IP samples, using two normalization methods. The orange and blue circles represent (to scale) the number of differential TEs identified using a "Bin correlation" and "Library size" normalization approach, respectively.
Figure 4:
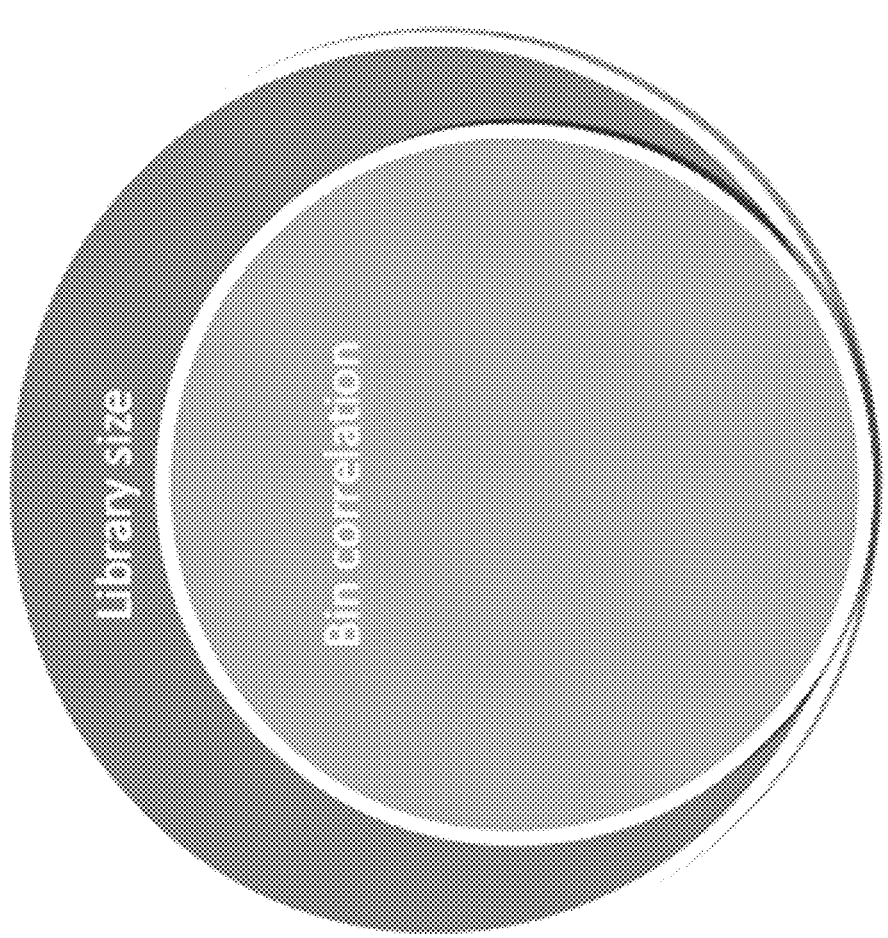
Figure 5:
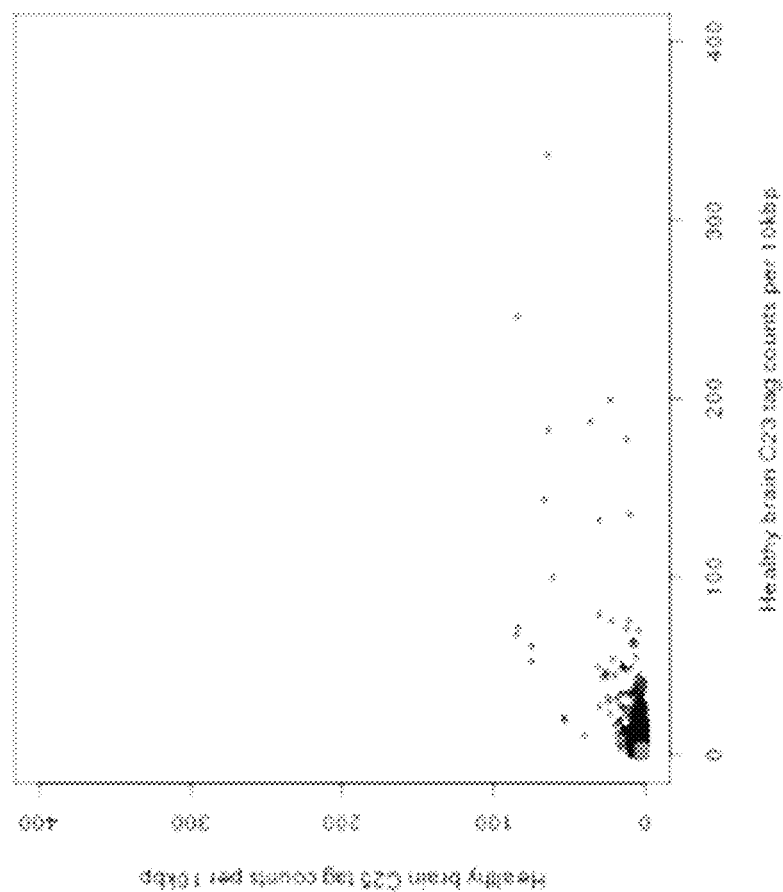
FIG. 5 is a pair of scatter plots showing separation of the whole genome into non-overlapping adjacent 10 Kbp bins. Each black dot represents read counts of a bin. Those bins selected to compute the normalization factors are depicted in gray (left). The plots shows read counts of TDP-43-IP and healthy control samples (left) and read counts of two human healthy brain samples from CLIP-seq data (right).
Figure 5:
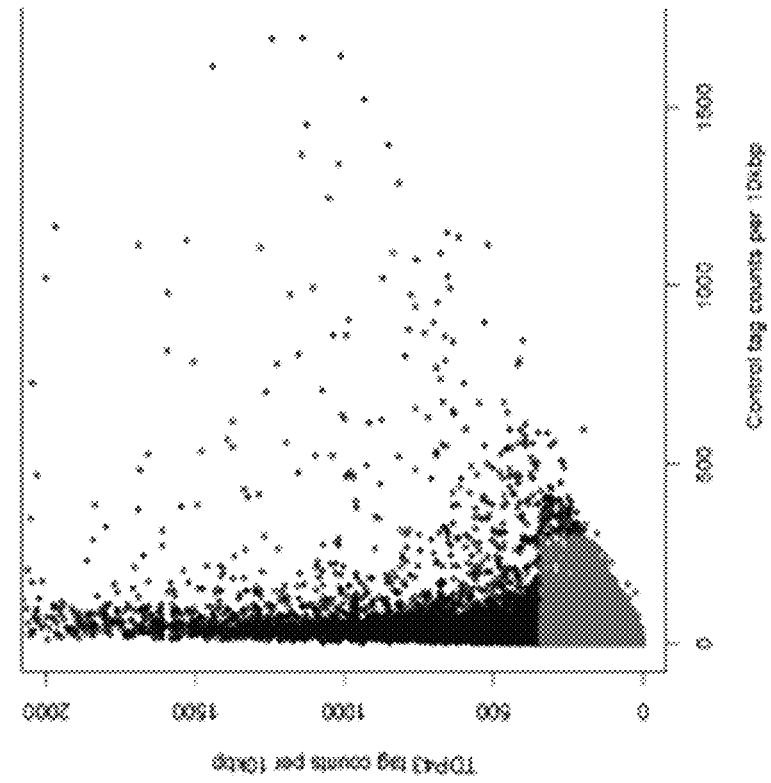

A bin correlation approach as described in PeakSeq (Rozowsky et al., 2009, Nat. Biotech. 27, 66-75) was used to normalize the libraries, after comparing it with the most widely used library size normalization method. FIG. 4 shows the comparison of the predicted differentially bound repeat elements. The bin correlation approach turned out to be more conservative than the library size method. The main reason is that in the control-IP sample, the total number of aligned reads is dominated by a few regions, mostly rRNA repeats, such that using library sizes as a normalization factor will cause a bias towards non-rRNA repeat regions in TDP-43-IP samples. To compute the bin correlation, the whole genome was separated into adjacent non-overlapping 10 Kbp bins. Then the number of reads overlapping with each bin was calculated for all libraries. Notice that each read (alignment) will only be counted once, and the count here is actually the weight of the alignment. Suppose that three reads with alignment weight 0.5, 1, and 0.5 fall in a bin b, then the count of b is 2 instead of 3. The library with the largest number of mapped reads was chosen as a reference. A linear regression was applied to bins of every other library against those of the reference. The correlation coefficient was used as the normalization factor, i.e., $Li \approx ei*Lr$ where $Lr$ is the reference library, $Li$ is one other library, and $ei$ is the correlation coefficient of library $Li$ to $Lr$. FIG. 5 shows the distributions of weighted bin counts between control-IP and TDP-43-IP samples from rat. The majority of bins with high values in either library show large differences, and these bins probably contain the true differential binding sites. These were excluded from the normalization procedure, and only the low abundance bins, colored red in FIG. 5 were used to estimate the background for library normalization. The underlying assumption is that the background of the two libraries is similar.

Differential Binding Analysis.

To identify potential differential binding sites of TDP-43, a sliding window with size of 500 bp and moving step size of 100 bp was used to scan the genome and compute the number of reads falling in the window in both samples. The reason for partially overlapping windows is to increase the resolution at which optimal peaks can be discovered. As described above, the counts in each bin are weighted by the number of loci to which they were mapped. For the rat data, the read counts were modeled with a Poisson distribution, similarly to two popular ChIP-seq analysis approaches, MACS (Zhang et al., 2008, Genome Biol. 9, R137) and PeakSeq (Rozowsky et al., 2009, Nat. Biotech. 27, 66-75). In the case of human data, in which each treatment has 3 biological replicates, an over-dispersed Poisson distribution (negative binomial distribution) was applied to model the read counts. In both cases, the p-value of the difference of the read counts was calculated as described in DESeq. Anders et al., 2010, Genome. Bio. 11, R106. Given a window wi with reads kiA and kiB from libraries A and B, and kiA+kiB=kiS, the p-value of (kiA, kiB) is the probabilities of all pairs with probabilities less than or equal to p(kiA, kiB) among all combinations, i.e., where $p(a, b)$ is $p(a)*p(b)$, by assuming the two libraries are independent, and $p(x)$ was computed using either the Poisson distribution or a negative binomial distribution.

The null hypothesis tested against a negative binomial model states that it is statistically unlikely for a combination of (1) random selection of transcripts sequenced and (2) biological variation between replicates to create a differential enrichment of reads within the given window that is larger than what was seen in the TDP-43 IP data as compared to the control. For the rat samples, which did not include replicates, the results were tested against a Poisson model null hypothesis that random selection of sequenced transcripts would be statistically unlikely to result in differential enrichment greater than what is seen in the data. These p-values were corrected for multiple hypotheses testing using the Benjamini-Hochberg correction. A significance threshold was set, adjusted p-value<0.00001, for identifying differentially enriched regions. Next, the sliding window was advanced by 100 bp and the previous step was repeated. Enriched regions with a gap of less than 500 bp and with the same direction for differential enrichment (i.e., both TDP-43 enriched or both depleted) were merged.

The above differential binding analysis method was used to analyze the datasets in three different ways. For the UNIQ method (UNIQ; see text), only uniquely mapped reads were included. For the UNIQ+SameEle method (UNIQ+SameEle; see text), unique reads and those that mapped to multiple locations were included, so long as they mapped to the same element. For the MULTI method (MULTI; see text), all mappable reads were included.

Annotations.

A predicted region was annotated as 'RefGene', if it overlaps with exons of a gene, or as 'repeat' if it overlaps with a repetitive element. If a differential binding site overlaps with a repeat region, but this repeat region is inside an exon, then the region will be annotated as the corresponding gene. Simple repeats that overlap with other repeat classes are not considered. The annotations were obtained from the UCSC genome website, as described above, which provides 4 levels of classification for most repeat elements: Class, Family, Element, and Instance. This nomenclature approximates that used by the RepBase group, from which these annotations were derived. Jurka et al., 2005, Cytogenet. Genome Res. 110, 462, 467. An example of that annotation information would be: Class I (retrotransposons), LINE/L2, L2b, chr1:23803-24038. Any cross-comparisons between datasets and species took place at the "Element" level (L2b in the above example), since TE instances (loci) are usually not conserved across evolutionarily distant species and, for the case of the loci that included multi-mapping reads, unambiguous identification of the particular locus from which the reads derived was difficult for many instances.

Motif Enrichment Analysis.

Figure 6:
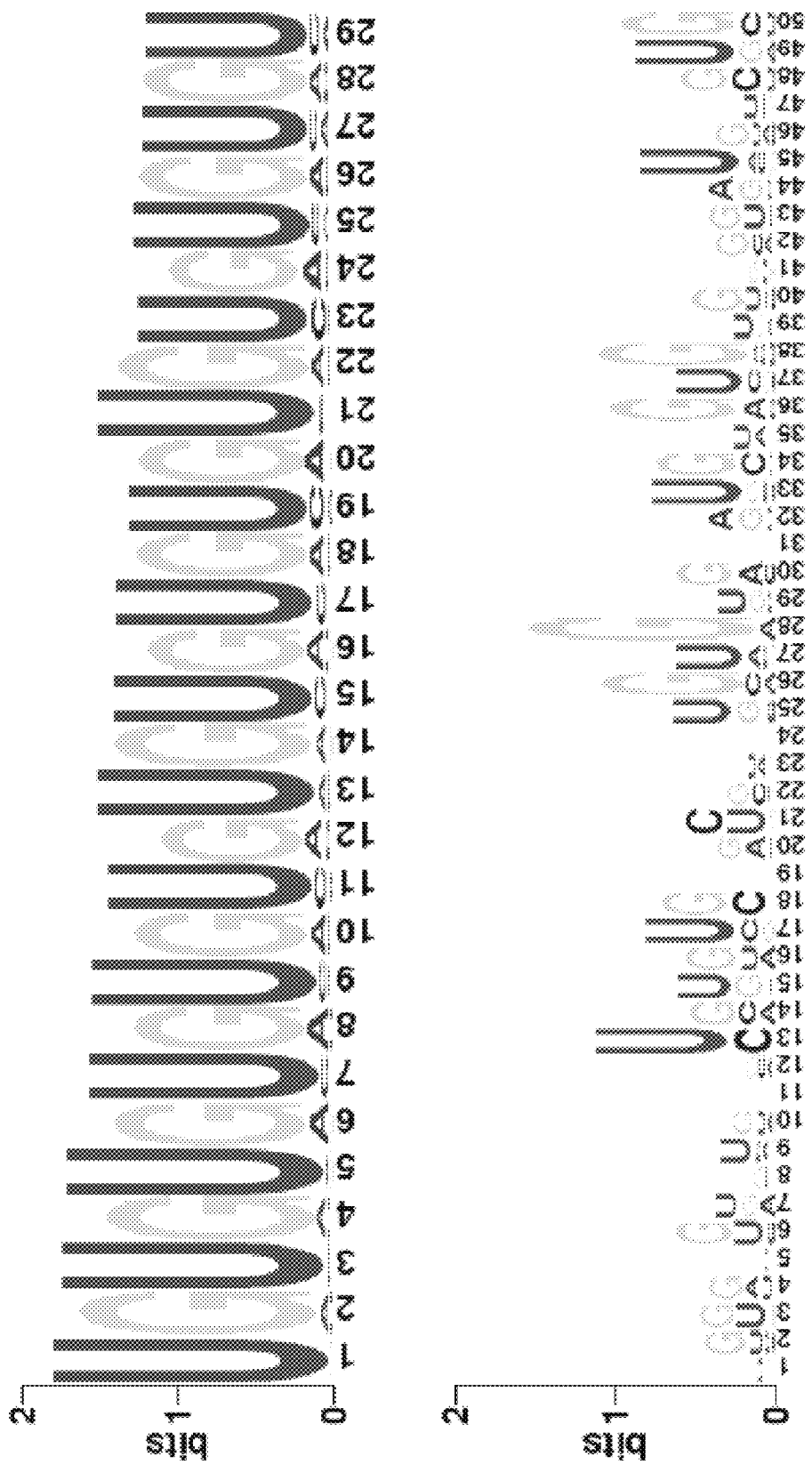
FIG. 6 depicts Motif logos for the most enriched motifs, as identified by MEME, in the TDP-43 binding peaks overlapping repetitive regions, based on the analysis of Rat RIP-seq data (top) and human CLIP-seq data from healthy brain tissue (bottom).

MEME (Machanick et al., 2011, Bioinformatics 27, 1696-1687) was used to identify the most enriched motifs of the TDP-43 binding sequences at repetitive regions, shown in FIG. 6. Both the distribution of each single nucleotide and dinucleotide were computed and used as the MEME background model. Analysis of the most enriched pentamer, UGUGU (Tollervey et al., 2011, Nat. Neurosci. 14, 452-458), on both genes and repetitive regions was performed in a similar way as described. Wang et al., 2010, PLoS Biol. 8, e10000530. The number of reads containing the pentamer at each nucleotide position surrounding the binding sites in a range of [−25 nt, 25 nt] was calculated and then normalized against randomized data. The control data (random data) was generated 100 times with randomly selected binding position sites.

To test the robustness of the enrichment difference in the library from subjects with FTLD samples, random samplings were performed in two ways. First, random samples of the healthy brain subjects were selected 100 times, to look for differential enrichment of the UGUGU motif among sub-samples of the healthy peaks. None of them show such a dip in motif enrichment. Second, 50% of the peaks from the healthy and FTLD brains were randomly selected, and RefGene/repeat motif enrichment ratios in these sub-samples were tested to estimate the sampling error on the estimated RefGene/repeat motif enrichment ratios.

Binding Site identification from Mouse CLIP-Seq Data.

The approach described above was not suitable to the mouse dataset, because of a lack of control samples. Therefore, a similar method (Wang et al, 2010, PLoS Biol. 8, e10000530) as used by the authors of the dataset was applied. As a control, CLIP cross-link nucleotide positions were randomly assigned to the reference genome. The significance of the cross-link sites were computed by comparing the observed probability of the abundance (cDNA counts) to the background frequency. The background frequency was obtained by iterating the randomization 100 times. The adjusted p-value for a cross-link site with cDNA counts x was computed as $padj(x)=(\mu x+\sigma x)/px$, where $\nu x$ and $\sigma x$ are the mean and standard deviation of frequency of cDNA counts x in the randomized background across 100 iterations, and px is the observed probability. This method is not as robust as that used for the rat and human peak identification due to the non-random rates of transcription in the genome. The p-values shown in Tables 3-6 reflect confidence that candidate binding sites are significant with respect to a model in which reads are otherwise randomly distributed genome-wide. Such a background model is known to be false for gene transcripts, but it is unclear the extent to which this model would fail for transcripts derived from repetitive element loci. At any rate, the lack of a control sample constrained an accurate estimate the background for this single dataset.

Results

Figure 1B:
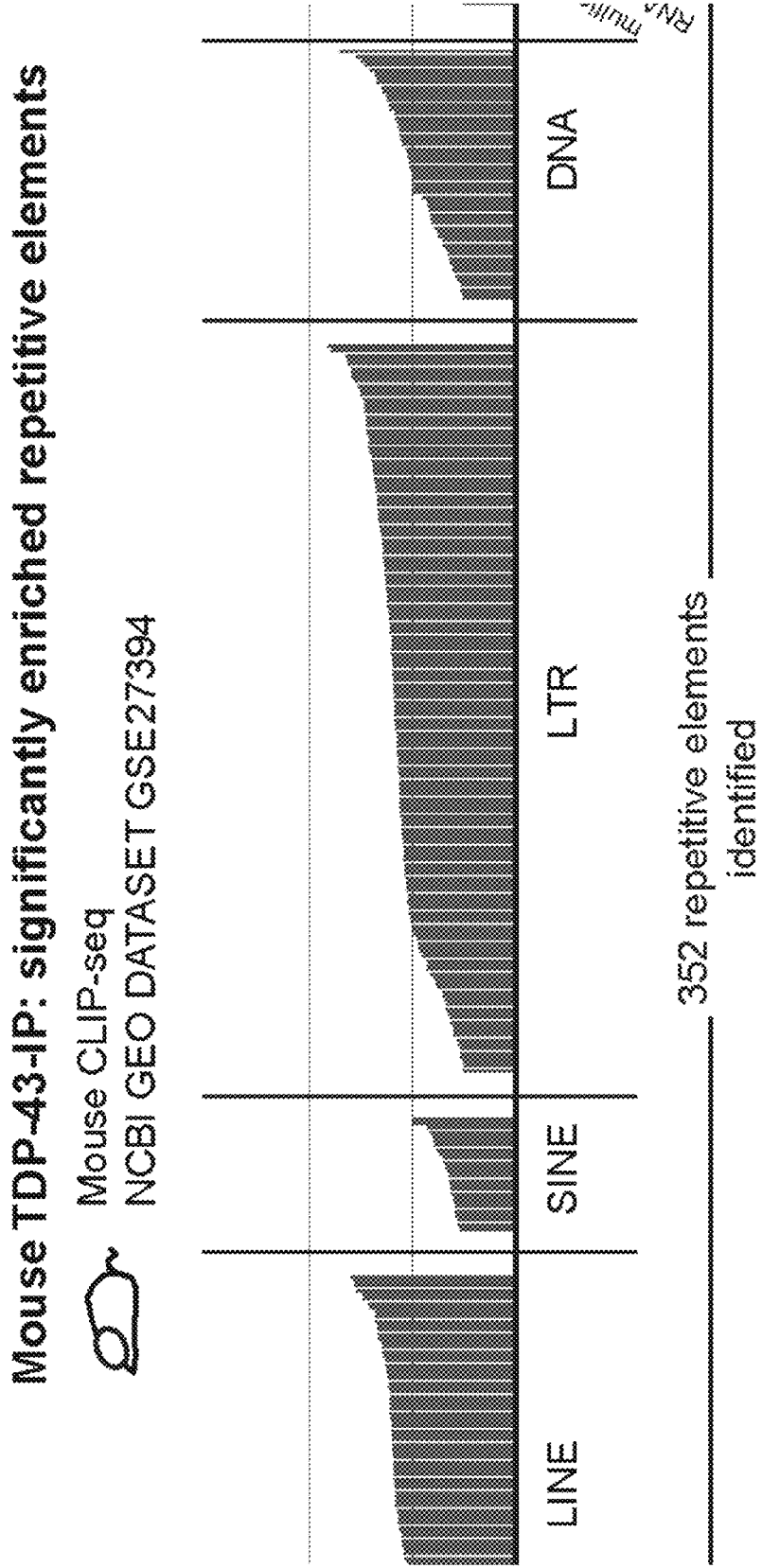

First, reanalysis was carried out on the raw data from the rat TDP-43 RNA immunoprecipitation sequencing (RIP-seq) dataset (Sephton et al, 2011, J. Biol. Chem. 286, 1204-1215), and from the mouse and human TDP-43 in vivo crosslinking-immunoprecipitation sequencing (CLIP-seq) datasets. Tollervey et al., 2011, Nat. Neurosci. 14, 452-458; Polymenidou et al., 2011, Nat. Neurosci. 14, 459-468). Three different analysis methods were tested to examine effects on TEs (FIGS. 1A-C; Methods; Tables 1-3). Because reads could potentially map to many regions, an analysis in which each location was weighted based on the number of alignments was first used (FIG. 1A-B; Methods). This analysis method (MULTI), which included both unique and multi mapped reads, assigns an enrichment level for each element, but does not distinguish contributions of individual instances of each element. Although this method can potentially include effects from TEs that are difficult to map with short read sequence, a disadvantage is that it does not distinguish which instances of a given TE are detected. In addition, because many TE copies are present within introns of genes, the MULTI method does not distinguish whether the TE sequences are co-expressed with genes or expressed from TEs per se.

Figure 1C:
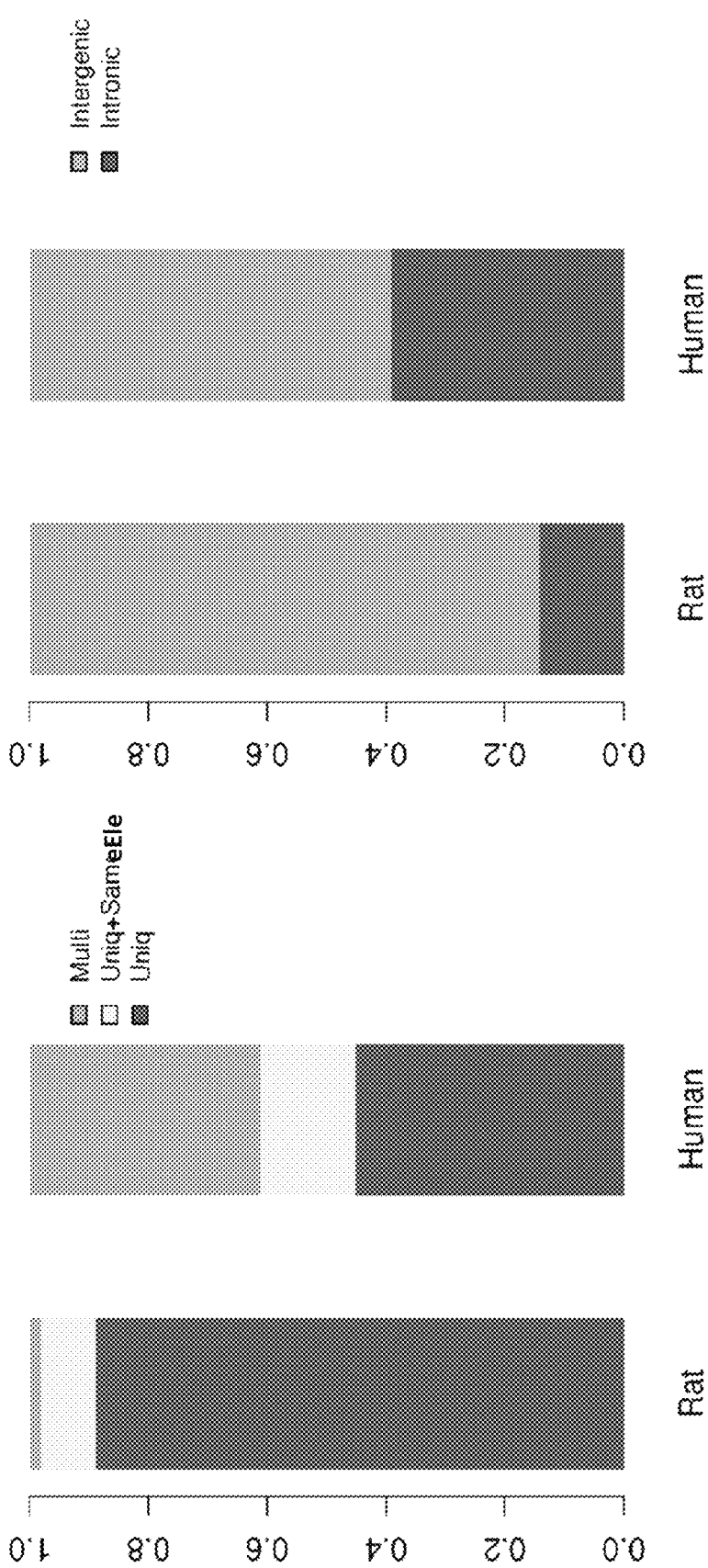
FIG. 1C is a bar graph showing: that the majority of TE targets identified with the MULTI method in rats are also identified with the UNIQ or UNIQ+SameEle method in rats (left panel, rats); that the majority of TE targets identified with the MULTI method that show reduced binding in tissue samples from human FTLD patients compared to healthy human controls are also identified with the UNIQ or UNIQ+SameEle method (left panel, humans); and that most rat TE targets and differentially bound human TE targets identified with UNIQ are intergenic (right panel).
Figure 8A:
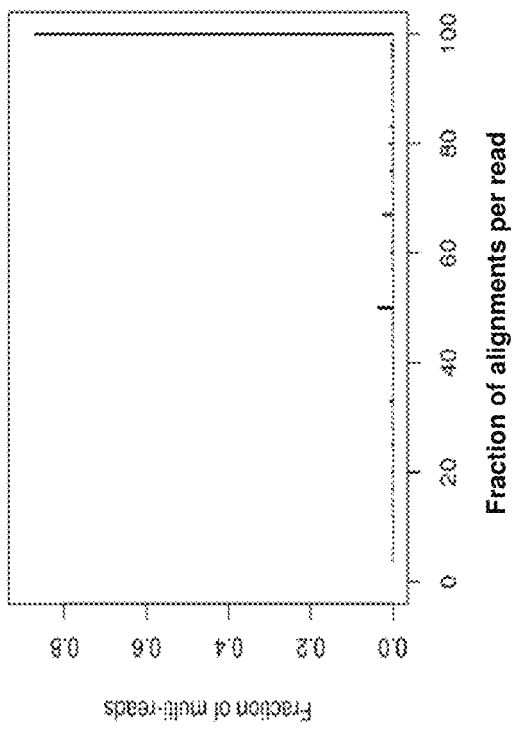
FIGS. 8A and 8B are panels showing the fraction of the most frequent TEs for each read having multiple alignments (multi-read) and the distribution of all multi-reads with different common TE alignment fractions. For about 80% of the multi-reads, all alignments corresponded to the same TE element in rats (8A), and about half of all alignments corresponded to same TE element in humans (8B).
Figure 8B:
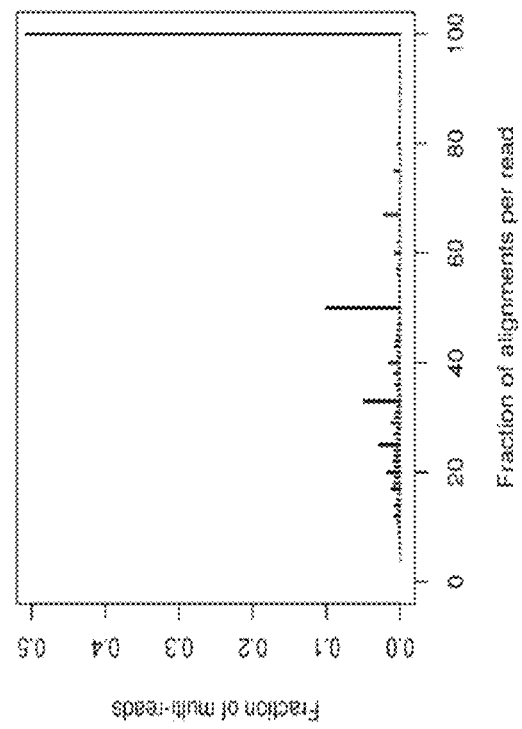
Figure 9A:
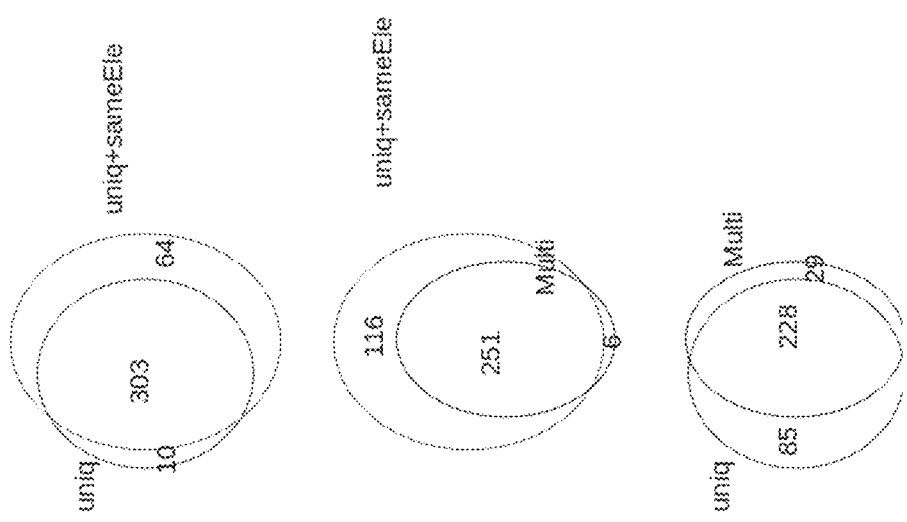
FIGS. 9A and 9B are sets of Venn diagrams showing the overlap of detected TEs for rats (9A) and humans (9B) among three mapping methods: UNIQ (uniquely mapped reads), UNIQ+SameEle (uniquely mapped reads and multi-reads mapped to the same elements), and MULTI (unique reads and multi-reads).
Figure 9B:
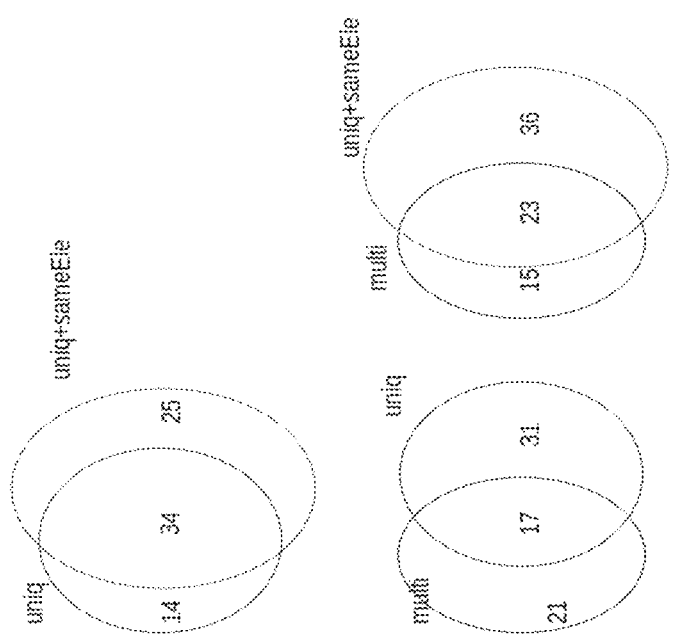
Figure 10A:
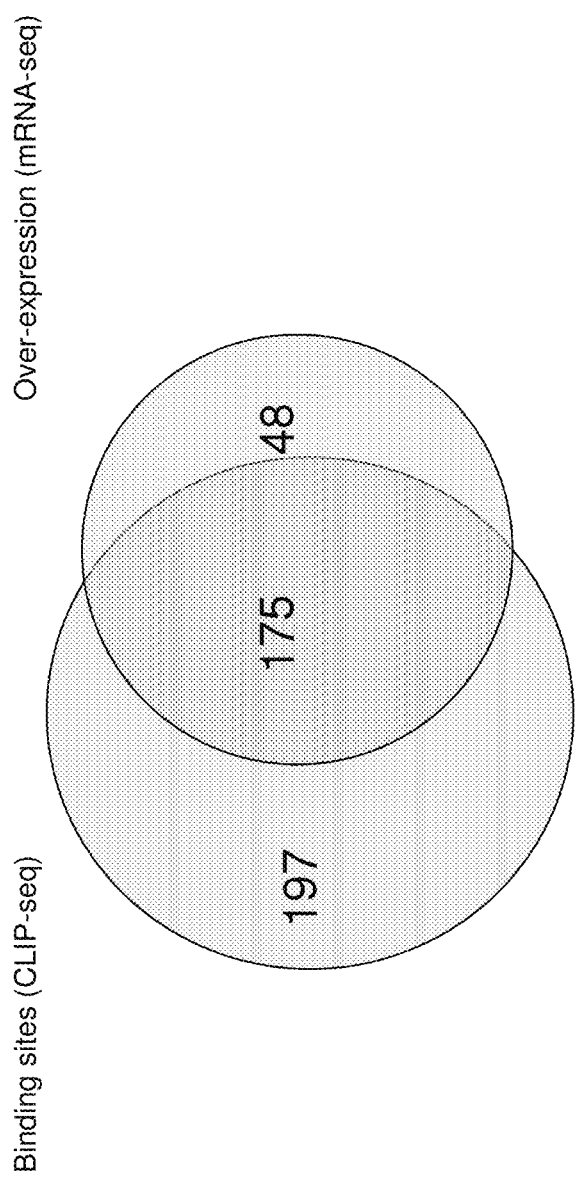
FIGS. 10A and 10B are sets of Venn diagrams showing the overlap between TDP-43 binding sites (CLIP-seq) with either TE transcripts induced by TDP-43 overexpression (10A) or RefGene transcripts induced by TDP-43 overexpression (10B).
Figure 10B:
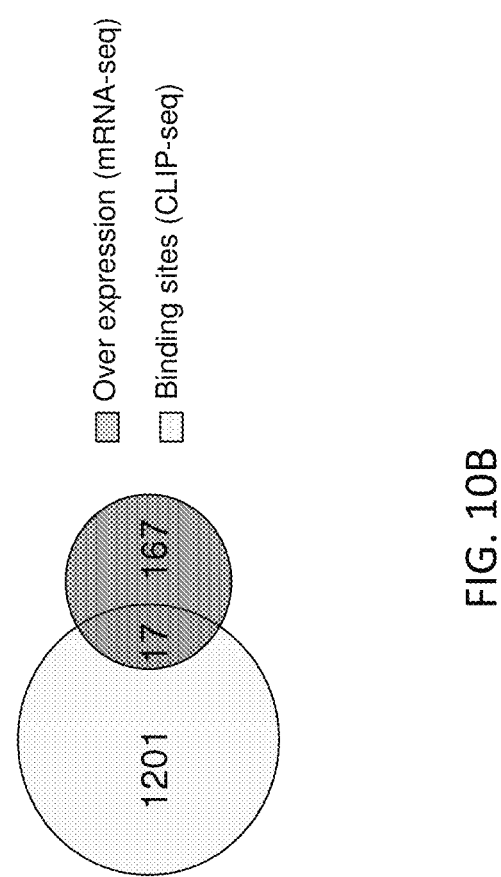

To address these issues, and to test the robustness of our observations, two additional mapping methods for the rat and human datasets were also tested (FIGS. 1C, 8, 9; Methods). First, only the subset of reads that map uniquely to the genome (UNIQ). Although this method does bias the results to the fraction of TEs that have diverged enough to have unique sequences, it provides confidence that the signal derives from unique chromosomal locations. As a third mapping strategy (UNIQ+SameEle), the effects of including both uniquely mapped sequences and those that map to multiple locations so long as they map to the same element were examined (weighted for their contribution to each instance as above—see Methods).

With all three mapping strategies, a dramatic enrichment of sequences that derive from each major class of TE was found (FIGS. 1A-C, 9; Table 3). With the MULTI method, we find 271 significantly enriched or depleted (most were enriched) repeat element sub-families in the rat TDP-43-IP samples versus control (FIG. 1A), of which 245 correspond to TEs. In the mouse dataset (FIG. 1B), MULTI detects significant enrichment of 352 repeat element sub-families of which 334 correspond to TEs (Table 3). These comprise all major classes of TEs, including LINE, SINE, LTR and some DNA elements (Hua-Van et al., 2011, Biol. Dir. 6, 19). For instance, 85 out of the 122 known mouse LINE elements and 6 out of the 7 known rat LINE elements are identified as TDP-43 targets. Similarly 26 out of 41 mouse SINE elements and 36 out of 37 rat SINE elements also were detected as TDP-43 targets. One caveat to the mouse clip-seq analysis was the lack of a control IP to use in estimating background counts for this single dataset, which could potentially lead to a larger false positive rate in the detected peaks (see Methods); however, the similarity in the results obtained for this dataset as compared to the well-controlled studies for rat (FIG. 1A) and human datasets (see below) argues for the inclusion of this dataset despite its caveats.

Overall, the most extensive binding to TEs was detected with the MULTI method. These findings are not an artifact of the way weights were assigned with the MULTI method. Even with the more restricted UNIQ analysis, ~80% of the rat elements that are differentially enriched when all mappable reads are included were identified (FIGS. 1C, 9). Moreover, among the uniquely mapped subset of TE instances that we identify as TDP-43 targets, greater than 80% map to intergenic regions rather than to elements contained within genes (FIG. 1C). When both unique mappers and multi mappers from the same element (UNIQ+SameEle) were included, enrichment for 95% of the TE sub-families that were identified as TDP-43 targets with the MULTI method (FIGS. 1C, 9) was detected.

The concordant results from these three different mapping strategies provide confidence that identification of TE derived transcripts as TDP-43 targets is a robust effect that is detected with a variety of methods for dealing with multi-copy elements.

As a test of the biological specificity of the finding that TDP-43 selectively binds to TE derived transcripts, the UNIQ mapping method was applied to a CLIP-seq dataset for an unrelated RNA binding protein. For this purpose, fused in sarcoma (FUS) was used, which like TDP-43, is an hnRNP RNA binding protein that plays diverse roles in RNA biology, including splicing (Da Cruz and Cleveland, 2011, Curr. Opin. Neurobiol. 21, 904-919). FUS is a relevant control for specificity, because like TDP-43 it is implicated in neurodegenerative disorders including ALS (Vance et al., 2009, Science 323, 1208-1211).

Figure 1D:
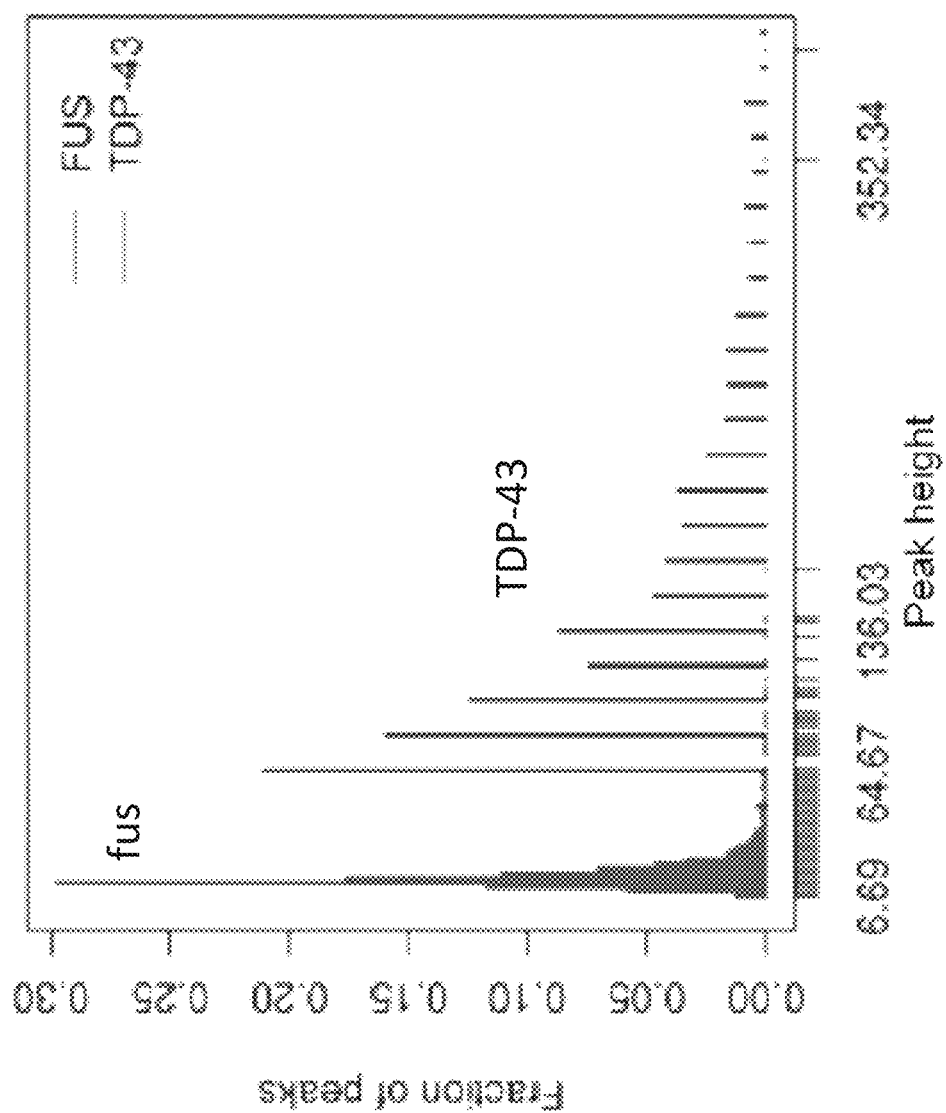
FIG. 1D is a bar graph comparing the peaks for TDP-43 and FUS targets, each identified by UNIQ+SameEle. Compared to FUS peaks, TDP-43 peaks are sharper and mean peak heights are greater (158 counts versus 17 counts).

The results with FUS are in stark contrast with TDP-43 (FIG. 1D). For TDP-43, the peaks that map to TEs are relatively large, with a mean height of 158 counts. However, for FUS, only small peaks map to TEs, with a mean peak height of 17 counts. The distributions of mean peak heights (see histogram, FIG. 1D) shows a clear separation between TDP-43 peaks and those obtained with FUS and this separation between peak heights is statistically significant (Wilcoxon rank sum p-value<2.2e-16).

Figure 11:
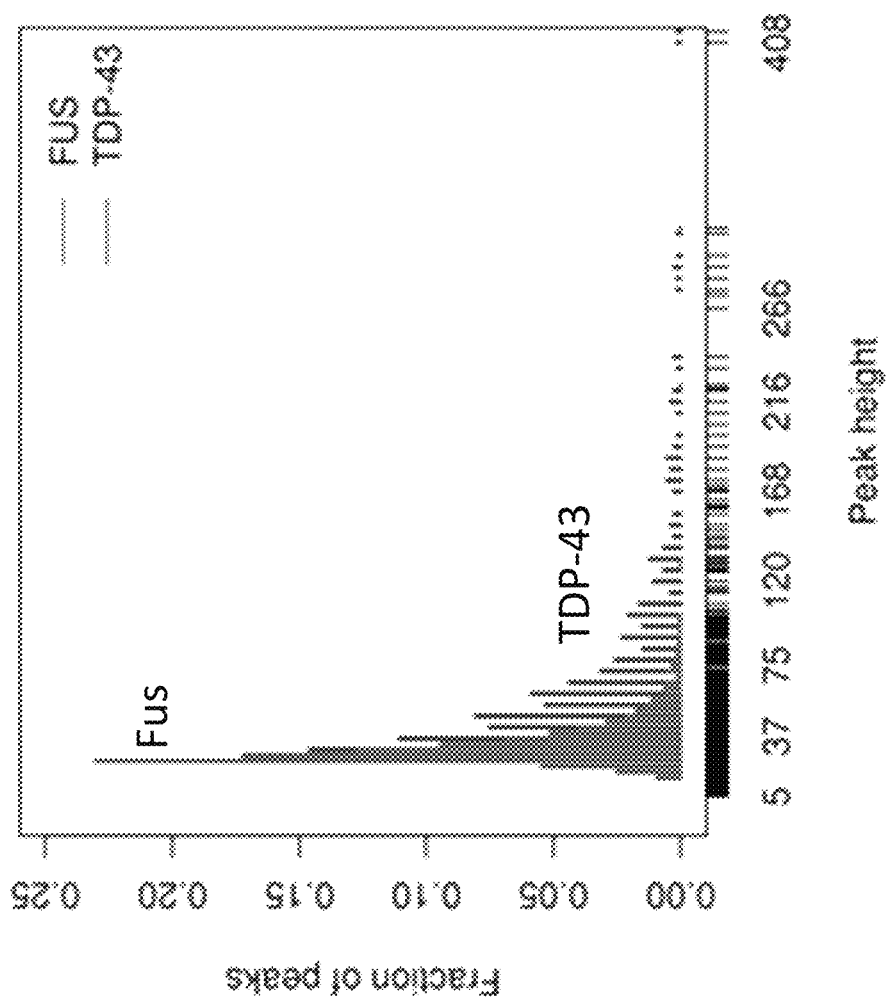
FIG. 11 is a histogram showing the distribution of peaks of RefGene targets for TDP-43 and FUS, using UNIQ+SameEle.

In contrast, the peaks that map over RefGene annotations using UNIQ+SameEle are similarly distributed for both FUS and TDP-43, with mean heights of 32 and 68 respectively. (FIG. 11). In addition, the separation between the TDP-43 and FUS peaks is less than 15 (p=0.98). The findings therefore show specificity for TDP-43—and are not a byproduct of inherent biases in library construction or analysis.

Figure 7A:
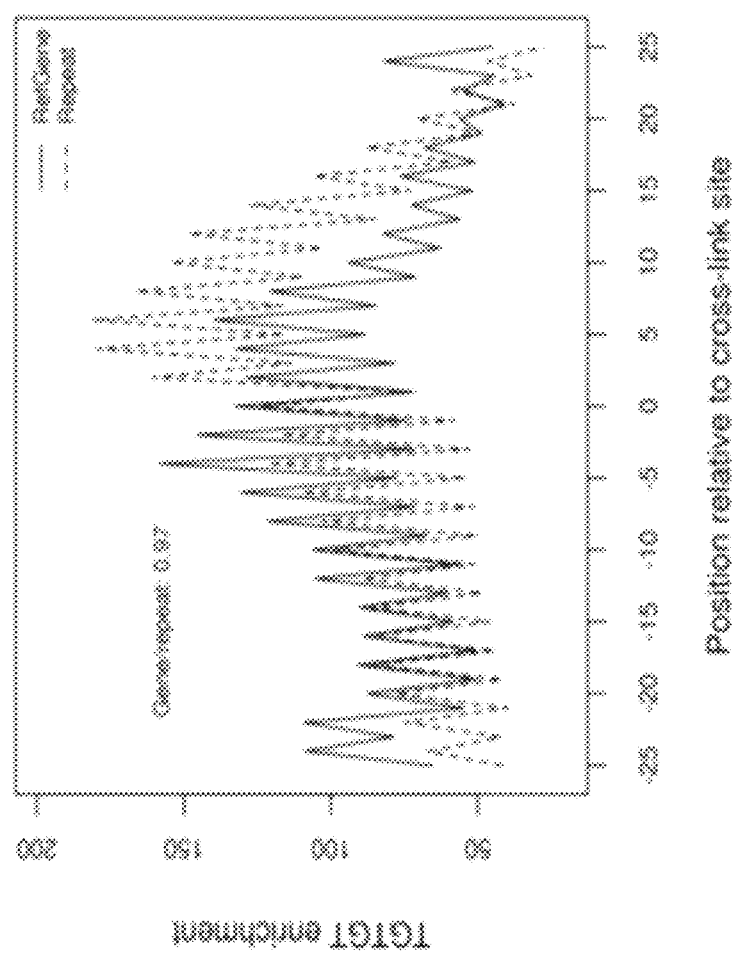
FIGS. 7A and 7B are panels showing enrichment in mice (7A) and rats (7B) among RefGene and repeat sequences for the UGUGU pentamer motif across a 51 nt window (−25 nt, 25 nt) surrounding the binding site.
Figure 7B:
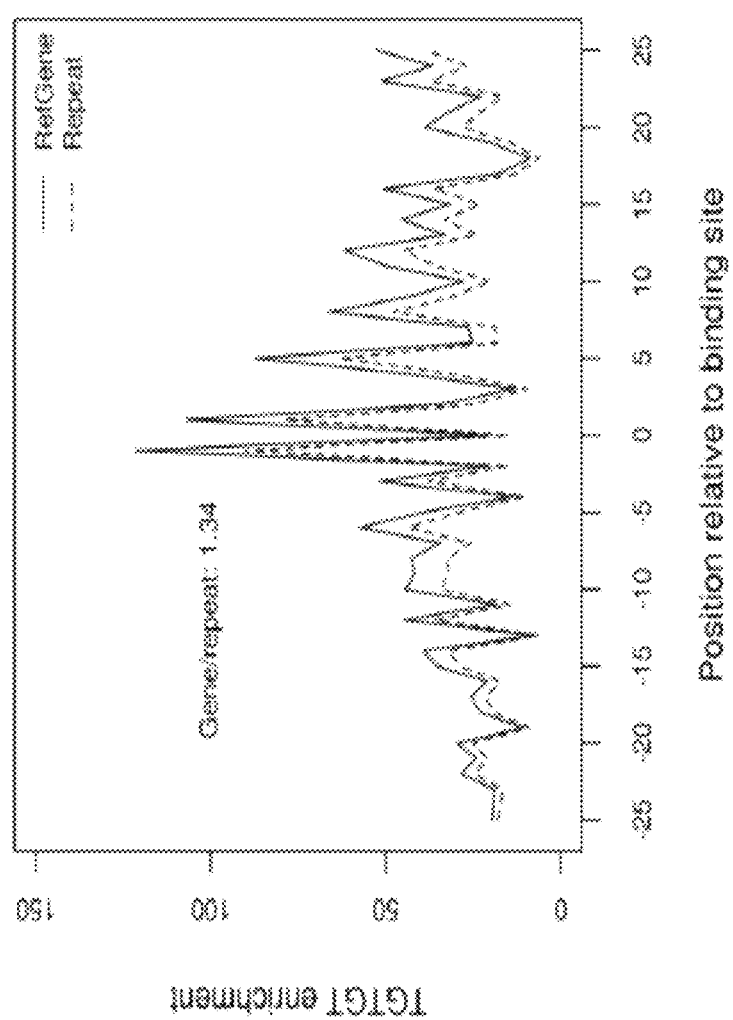

Because TDP-43 has a known binding motif among its mRNA targets, MEME (Machanick et al, 2011, Bioinformatics 27, 1696-1687; Methods) was used to identify enriched motifs among both the RefGene and repetitive targets. A UGUGU pentamer motif was identified that is equivalently enriched in uniquely mapped and repetitive targets (FIG. 7). This motif is consistent with the binding specificity of TDP-43 that has previously been observed for uniquely mapped sequences. See, e.g., Sephton et al., 2011, J. Biol. Chem. 286, 1204-1215; Tollervey et al., 2011, Nat. Neurosci. 14, 452-458; Polymenidou et al., 2011, Nat. Neurosci. 14, 459-468; Shan et al., 2010, Proc. Natl. Acad. Sci. USA 107, 16325-16330). Thus TDP-43 binds TE derived transcripts via a similar sequence motif as identified for RefGene targets.

In sum, the results shows that TDP-43 broadly targets TE-derived transcripts, including LTR retrotransposons, non-LTR retrotransposons (e.g., SINE, and LINE classes), and DNA mobile elements.

Example 2

TDP-43 Binding to TEs is Selectively Lost in FTLD Patients

Because the human dataset (Tollervey et al., 2011, Nat. Neurosci. 14, 452-458) includes samples from healthy and FTLD patients (which exhibit TDP-43 positive cytoplasmic inclusions), it also provided an opportunity to identify differences in the TDP-43 targets between FTLD and healthy controls in human samples.

Figure 12:
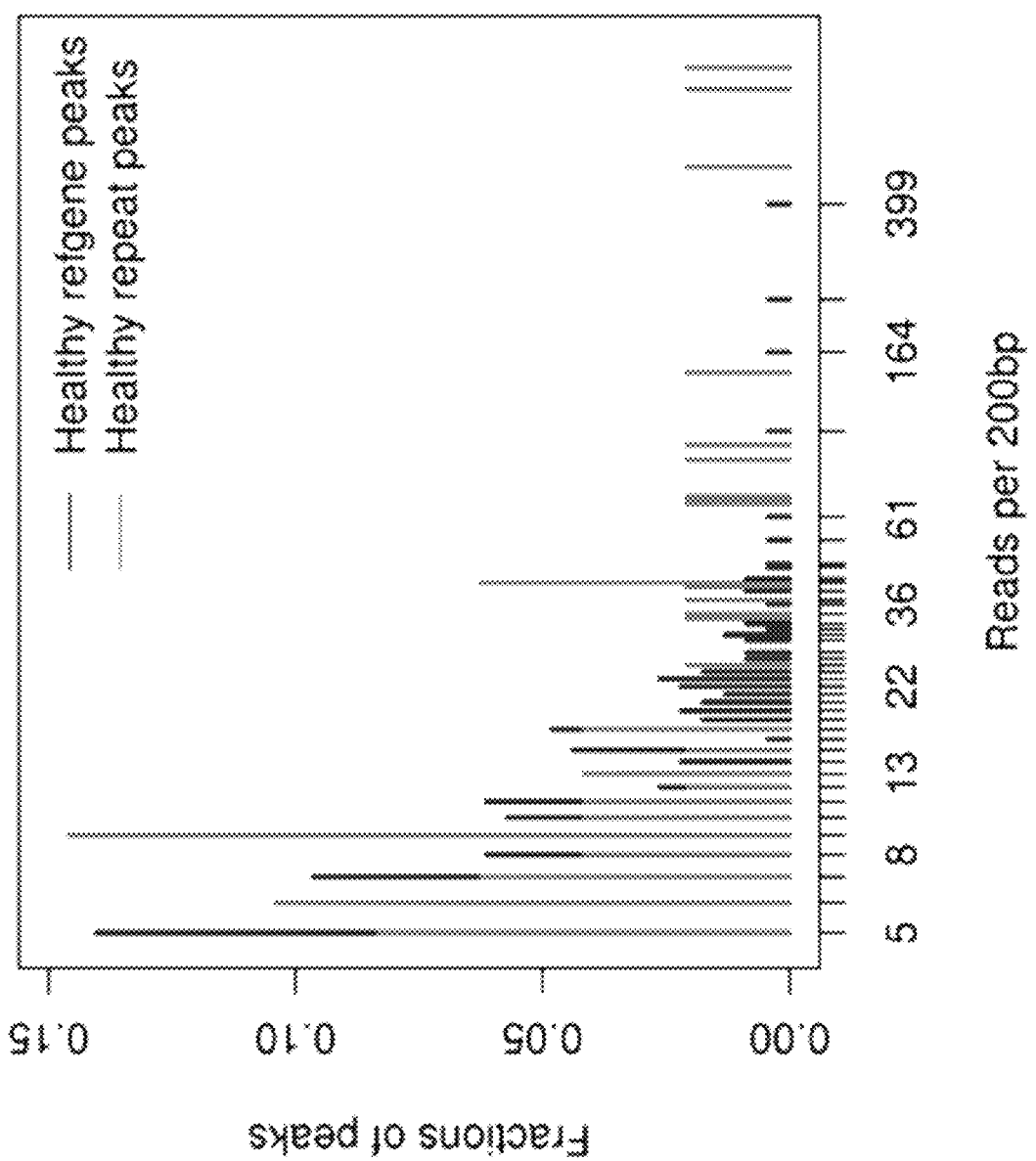
FIG. 12 is a histogram showing that for RefGene and repeat sequences that bind to TDP-43 in tissue from healthy human subjects, the distributions of peak heights are not significantly different from each other.

As in rat and mouse, a dramatic and significant enrichment in target sequences that derive from many classes of TEs was observed in human samples. As with the mouse and rat data, the distribution of peak heights for TE and RefGene targets of TDP-43 are similar (FIG. 12), indicating that the targeting of TE transcripts is as robust as it is for RefGene targets.

More striking, however, is the comparison between healthy subjects and FTLD patients. When the relative enrichment for each repeat element within healthy vs. FTLD samples was examined, a dramatic difference in binding to TE derived RNAs was detected (FIG. 1E-H). Overall, the association between TDP-43 and TE transcripts is significantly reduced in FTLD patients, which leads to a relative enrichment of 38 repeat elements in healthy versus FTLD, 28 of which correspond to transcripts derived from TEs (FIG. 2 and Tables 3-6; See Methods for statistical analyses). Reduced binding of TDP-43 to transcripts from all major classes of TE including SINE, LINE, LTR and a few DNA elements was shown. Here too, it was observed that the majority of the TE targets whose binding to TDP-43 was reduced in FTLD are consistently identified with all three methods (FIG. 1C). Most of the TE targets that show reduced binding to TDP-43 in FTLD samples are intergenic rather than contained within genes (FIG. 1C). Example peaks can be shown for one RefGene control as well as two differentially targeted TEs.

Figure 2A:
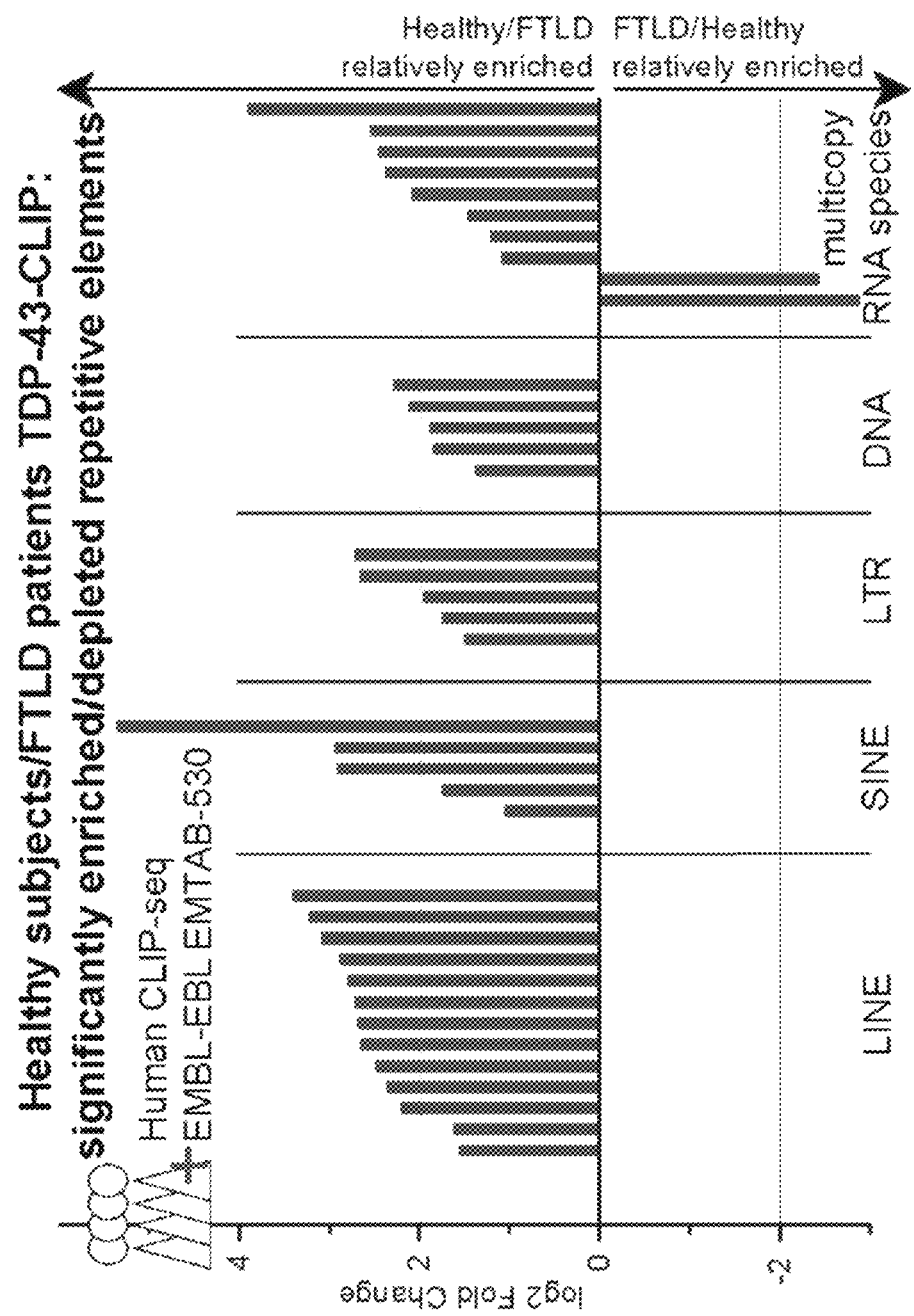
FIG. 2A is a histogram showing that TDP-43 binding to TEs is selectively lost in FTLD patients. In the human CLIP-seq data from FTLD patients versus healthy controls, significant changes in 38 repeat elements showed significant changes in differential binding (p<0.05; >2-fold change). Log 2-fold binding differences are shown for significant changes.
Figure 2B:
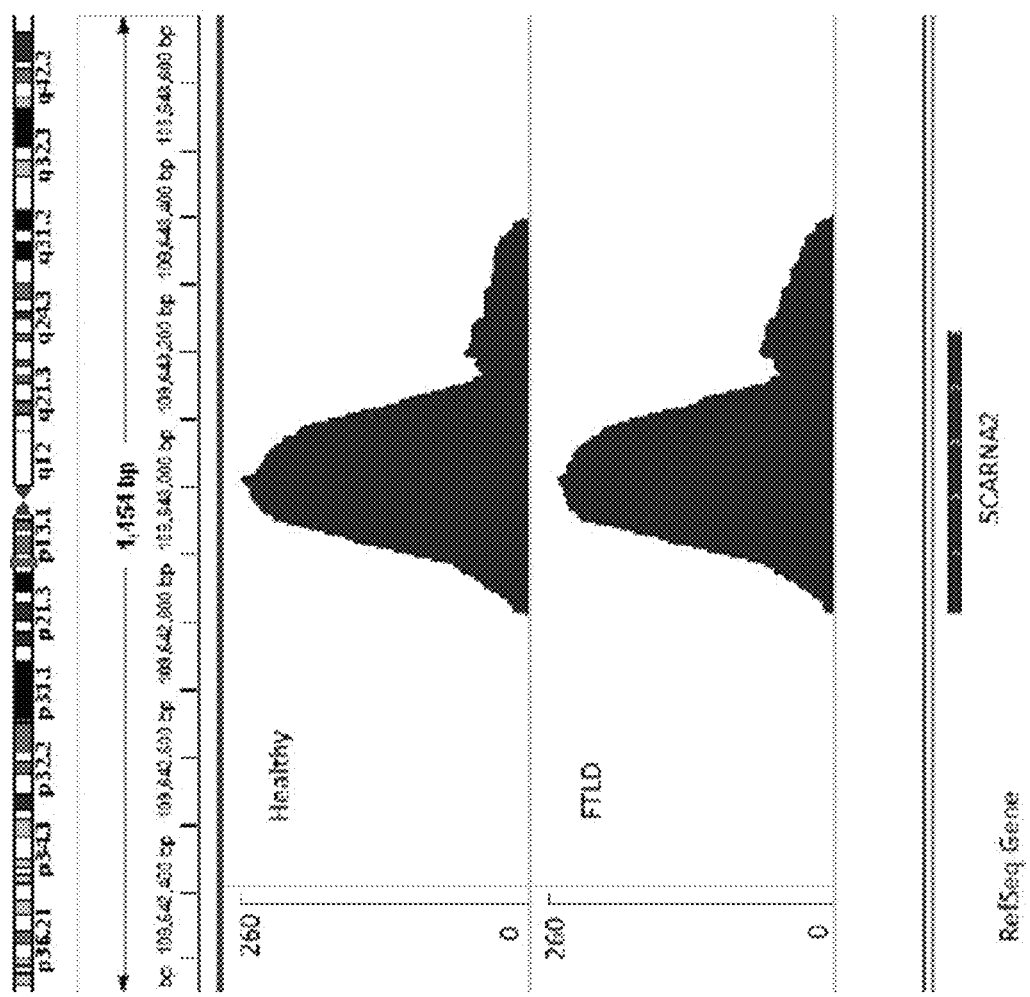
FIGS. 2B, 2C, and 2D are graphs showing peaks in Genome Browser from FTLD patients versus healthy human controls for one RefGene control (B) and two differentially targeted TEs (C, D).
Figure 2C:
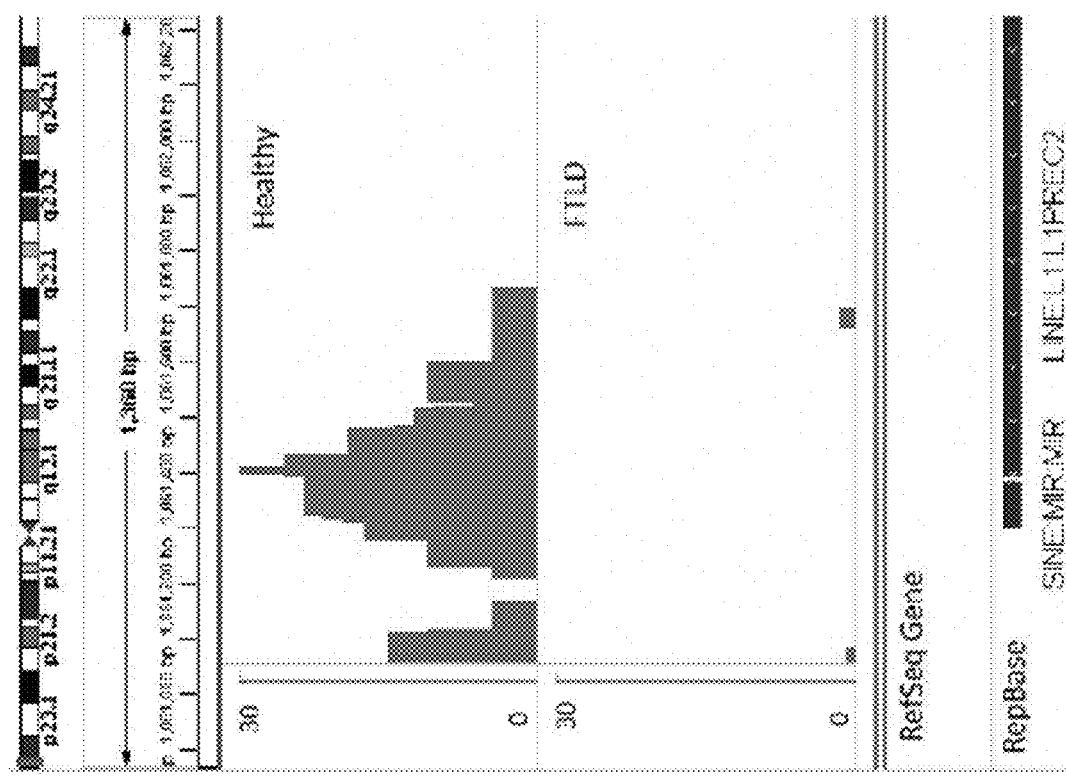
Figure 2D:
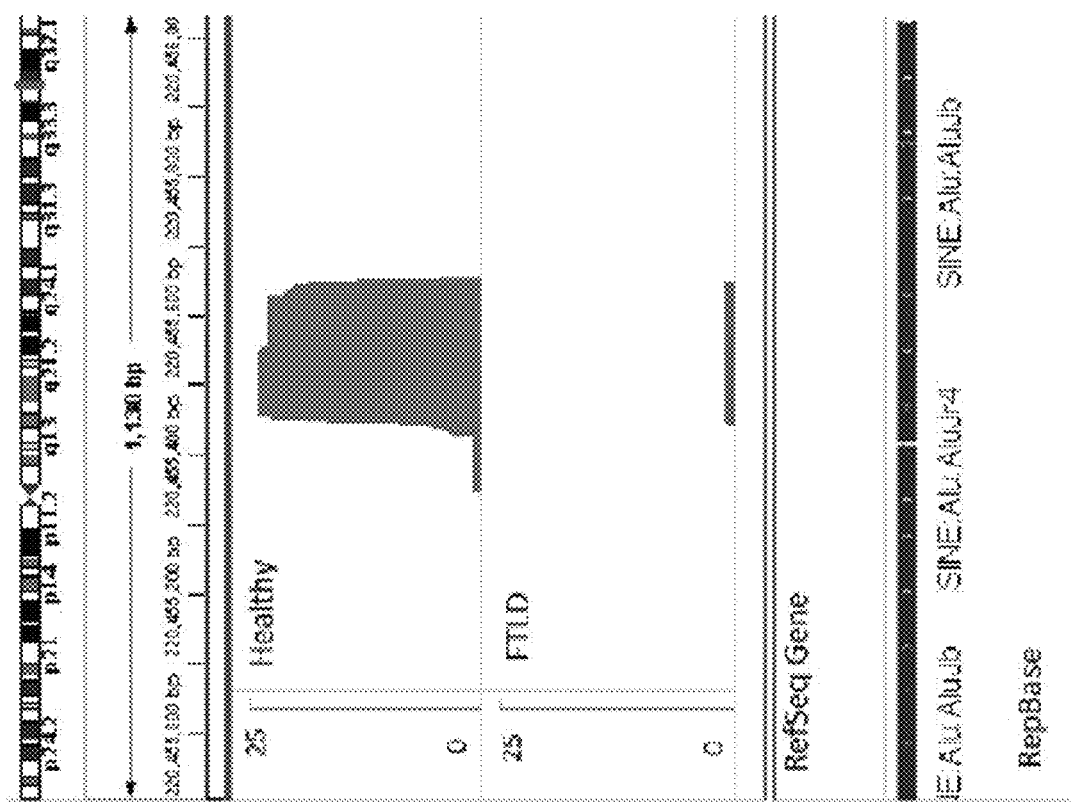
Figure 2E:
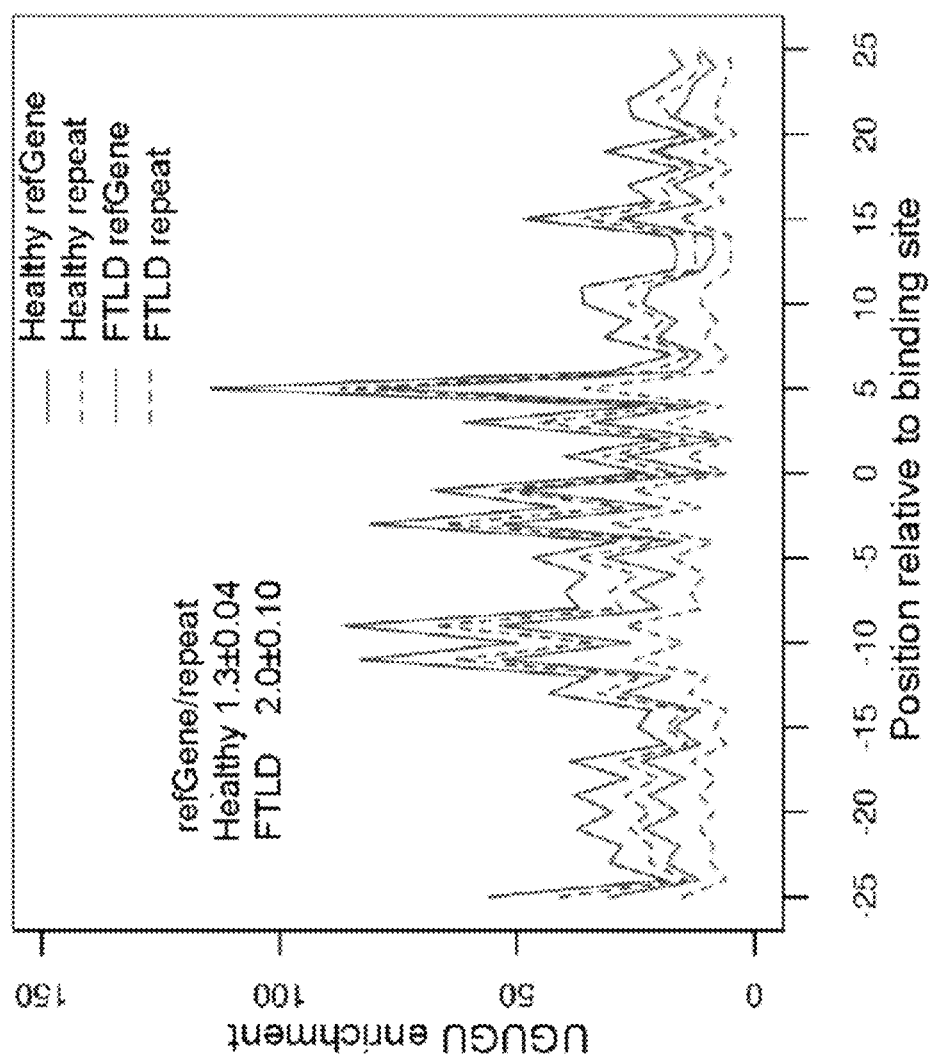
FIG. 2E is a graph showing that for RefGene and repeat sequences in healthy and FTLD tissue samples, the UGUGU motif in a 51-nt window surrounding the motif (−25 nt, 25 nt) is enriched, relative to the genome. Whereas motif enrichment of RefGene sequences is similar to that of repeat sequences in healthy samples (enrichment ratio≈1.3), it is greater than that of repeat sequences in FTLD patients (enrichment ratio=2.0, p<0.01).

This reduced binding in FTLD patients of TDP-43 to TE-derived transcripts also is apparent when over-all enrichment for the UGUGU pentamer motif (FIG. 2E) relative to the genome was examined. In the rat and mouse samples as well as in the dataset from healthy human brain samples, equivalent enrichment of UGUGU binding motifs among uniquely mapped (RefGene) versus repetitively mapped (repeat) TDP-43 targets (RefGene/repeat enrichment ratio near 1.0; FIG. 7; see Methods) was observed. In the FTLD-TDP-43-CLIP samples enrichment for the UGUGU motif among RefGene targets that is equivalent to that seen in healthy subjects was shown (FIG. 2E). However, the level of enrichment for this UGUGU motif was significantly lower among the sequences that map to repeat elements. In the FTLD samples, the RefGene/repeat enrichment ratio is increased to 2.0 (FIG. 2E; p-value<=0.01, p-values were assigned with 100 iterations on randomly chosen sets containing 50% of original data; see Methods). In other words, FTLD samples exhibit a selective reduction of binding to TE transcripts and also exhibit reduced UGUGU motif enrichment among the remaining repetitive sequences that still co-purify with TDP-43. This difference in motif enrichment between FTLD and control samples is only manifested among repeat annotations.

In sum, these studies show that the association between TDP-43 and many TE-derived RNA targets is reduced in FTLD patients relative to healthy subjects, indicating that the loss of TE control plays a role in the disease pathology.

Example 3

Animal Models of TDP-43 Dysfunction Reveal Broad Over-Expression of TE-Derived Transcripts The reduced binding of TE transcripts in FTLD patients suggested that TDP-43 pathology might include a loss of TE regulation. This possibility was explored in two ways: first, by analyzing the repetitive sequence reads from two different mRNA-seq datasets from mouse models of TDP-43 pathology; and second, by comparing the aberrantly elevated transcripts in the mRNA seq studies with the targets identified as targets of TDP-430, as shown in Example 1.

Methods mRNA-Seq Analysis.

RNA short sequences were aligned to the whole genome in order to assess the RNA profiles of repetitive elements. The alignment software and most of the parameter settings were the same as that used for aligning the CLIP-seq datasets (described above, except -m 200 was used in this case). The same weighting scheme was applied to each alignment as described above. Read abundances of a repeat element were computed by summing up the alignment weight of all reads mapped to the correct strand, within the TE annotation boundaries, and normalized by the length of that element. DESeq (Anders et al., 2010, Genome. Bio. 11, R106) was then used to detect differential abundances for repeat elements between control and TDP-43 manipulated samples.

Results

Figure 3A:
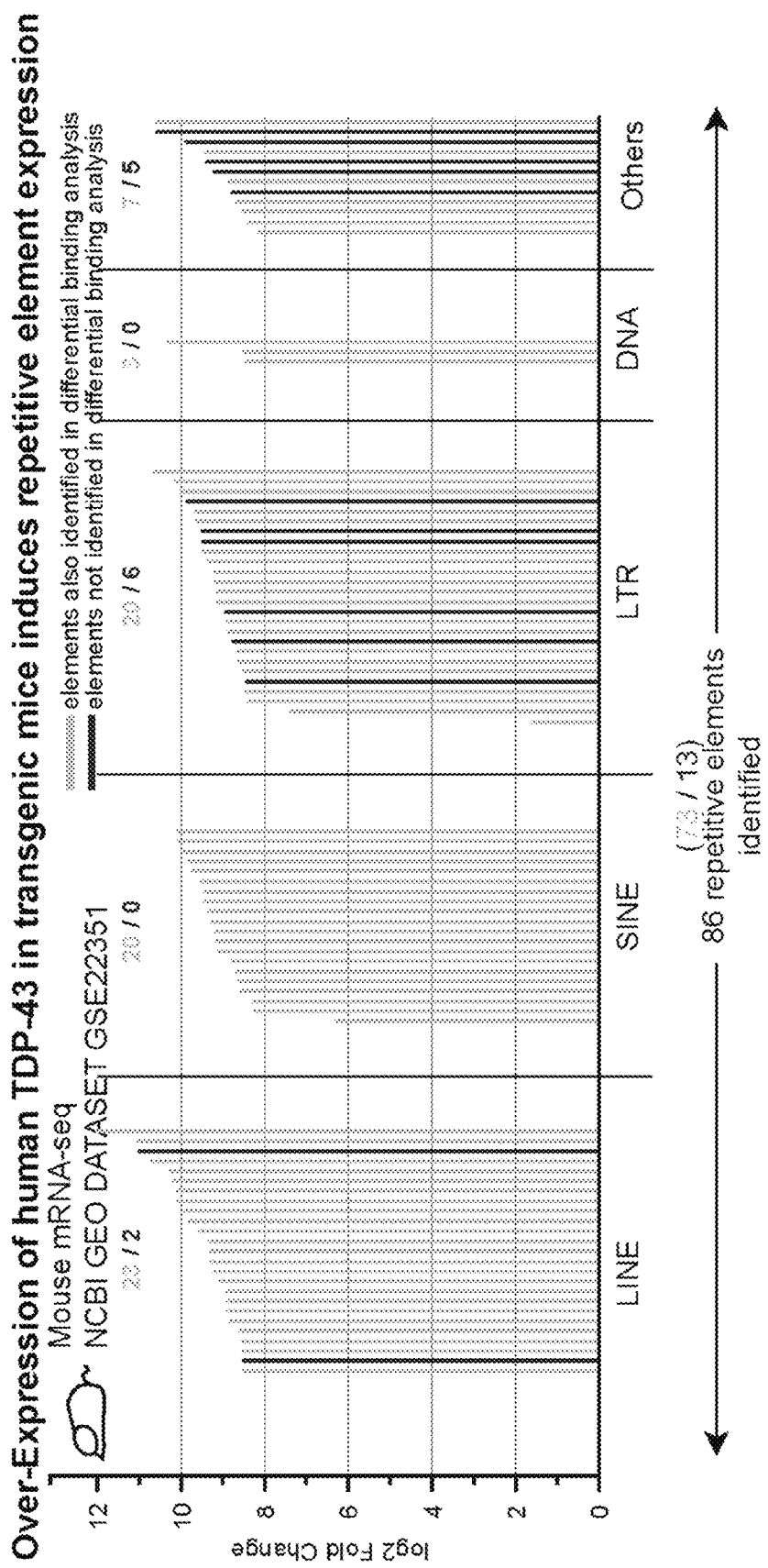
FIG. 3A is a histogram showing that over-expression of human TDP-43 in transgenic mice induces elevated expression of many TE-derived transcripts.
Figure 3B:
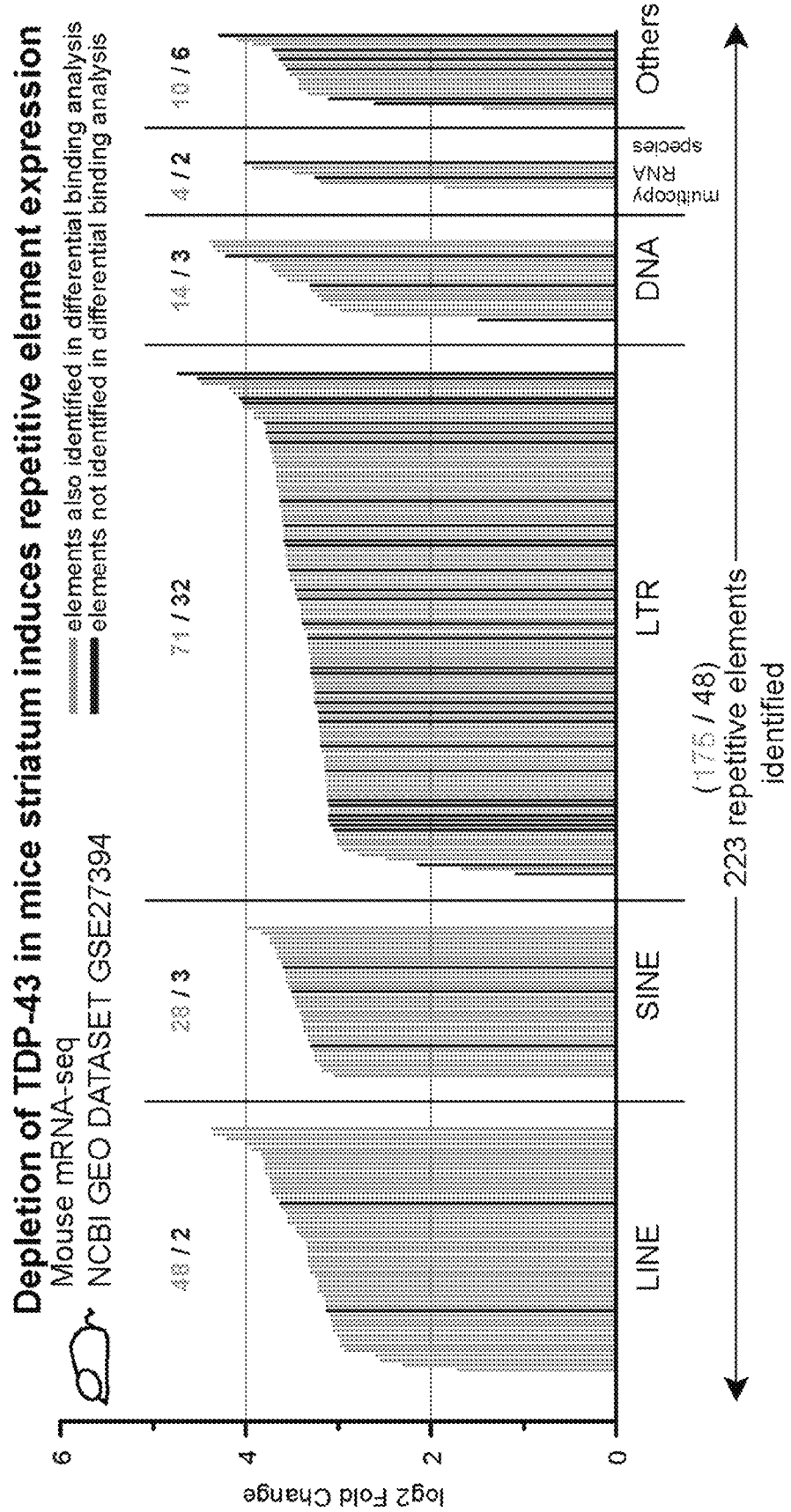
FIG. 3B is a histogram showing that depletion of TDP-43 in the mouse striatum results in increased expression of many TE-derived transcripts.

The first mRNA-seq study analyzed (Shan et al., 2010, Proc. Natl. Acad, Sci. USA 107, 16325-16330) used overexpression of human TDP-43 in transgenic mice. Overexpression of this aggregation prone protein is associated with toxic TDP-43 pathological effects and is thought to act as a dominant-negative, causing reduction in the normal functions of TDP-43. The second mRNA-seq study (Polymenidou et al., 2011, Nat. Neurosci. 14, 459-468) used antisense oligonucleotide-mediated depletion of TDP-43 in mouse striatum to test the effects of TDP-43 loss of function. Both studies identified transcripts that are differentially expressed or spliced in response to these TDP-43 manipulations. To ask if the above TDP-43 depletion and over-expression/dominant-negative impacted TE derived transcripts, sequence reads were again analyzed, including those that map to multiple locations. Broad elevations of TE derived transcripts were found in both the over-expression transgenic mouse model and in the striatal depletion of TDP-43 (FIG. 3). TDP-43 over-expression was associated with elevated expression of 86 repetitive elements (FIG. 3A), whereas TDP-43 depletion results in increased expression levels of 223 repetitive element species (FIG. 3B). In both cases, most of these correspond to LINE, SINE and LTR elements.

Figure 13:
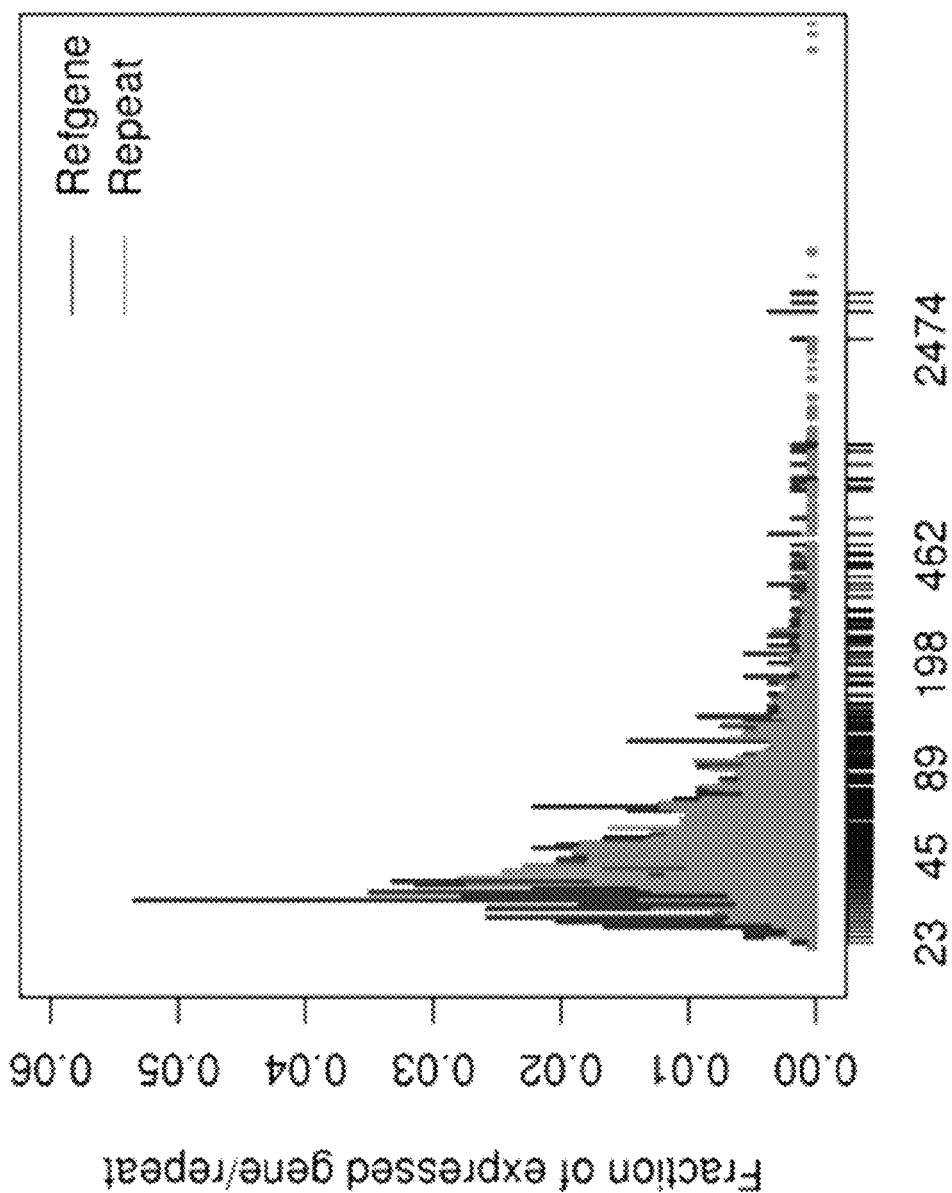
FIG. 13 is a histogram showing that the distributions of expression levels for RefGene and repeat sequences from the mouse TDP-43 overexpression dataset are not significantly different from each other.

Overall, the affected TE transcripts are expressed at levels comparable to those of the differentially expressed RefGene transcripts (FIG. 13), suggesting that these are robust effects on transcripts whose expression levels are not at the limit of detection. More importantly, when TDP-43 function is compromised, a striking degree of concordance between the TE transcripts that are elevated and the ones that we identified as RNA targets of TDP-43 in normal tissue was observed (Red in FIG. 3; Tables 3-6). Indeed the majority of elevated TE transcripts in both mouse mRNA-seq datasets also were detected as TDP-43 targets in the iCLIP-seq binding dataset (FIG. 3; Tables 3-6).

This remarkable concordance between the transcripts that are targeted by TDP-43 and those that are elevated in response to TDP-43 misexpression is unique to the repetitive elements in the genome. In contrast, CLIP targets identified from the RefGene fraction of the transcriptome have little overlap with those that show over-expression when TDP-43 function is compromised suggesting that the coding gene expression increases are largely indirect effects. Polymenidou et al., 2011, Nat. Neurosci. 14, 459-468. RefGene transcripts whose expression is reduced show good concordance with direct target identification.

In sum, these findings extend the observations in Examples 1 and 2: First, the findings reveal broad over-expression of TE derived transcripts in each of two different mouse models with TDP-43 dysfunction. Moreover, there is a striking overlap between the TE targets identified followed TDP-43 misexpression in animal studies and those identified in the CLIP study (FIGS. 2A-C, 10). Hence, a large fraction of the TEs to which TDP-43 binds become de-repressed in mouse TDP-43 disease models.

More generally, the studies described Examples 1-3 indicate that TDP-43 normally functions to silence or regulate TE expression. When TDP-43 protein function is compromised, TEs become over-expressed. Without being limited, unregulated TE expression may lead to pathological effects through increased transposition and through mechanisms other than increased transposition. Such mechanisms may include genome instability and the accumulation of mutations, DNA-damage dependent apoptosis, the induction of stress responses, adverse effects from accumulation of TE-derived RNAs or proteins, host responses to viral infection, increased episomal mobilization of TE derived RNAs and proteins, and cell death. Such toxicity from activation of mobile genetic elements can therefore contribute to TDP-43-mediated neurodegenerative disorders (and other disorders).

While certain embodiments are described herein, it will be understood that the described embodiments are not intended to limit the scope of the invention as defined by the appended claims. On the contrary, the present disclosure is intended to cover alternatives, modifications and equivalents that may be included within the spirit and scope of the invention as defined by the appended claims. Furthermore, certain details in the present disclosure are provided to convey a thorough understanding of the invention defined by the appended claims. However, it will be apparent to those skilled in the art that certain embodiments may be practiced without these details. In certain instances, well-known methods, procedures, or other specific details have not been described to avoid unnecessarily obscuring aspects of the invention defined by the appended claims.

What is claimed is:

1. A method of treatment, comprising
administering to a subject having a TDP-43 associated neurodegenerative disorder a transposon inhibitor in an amount effective to reduce the expression level of a transposon,
wherein the TDP-43 associated neurodegenerative disorder is frontotemporal lobar degeneration (FTLD).

2. The method of claim 1, further comprising testing for the presence of a TDP-43 associated cytoplasmic inclusion in the subject.

3. The method of claim 1, wherein the transposon inhibitor is an inhibitor of a protein encoded by a transposon.

4. The method of claim 3, wherein the protein encoded by the transposon is a transposase; an integrase; a reverse transcriptase; an endonuclease; a protein encoded by gag, pol, or env; an enzyme encoded by ORF1, or an enzyme encoded by ORF2.

5. The method of claim 1, wherein the transposon inhibitor is an anti-retroviral drug; an inhibitor of reverse transcription; an inhibitor of transposase or integrase activity; an inhibitor of endonuclease activity; a stimulator of DNA repair machinery; a zinc-finger that targets a transposon promoter region; a repressor that inhibits a transposon; an innate antiretroviral resistance factor; a small interfering RNAs (siRNA), short hairpin RNA (shRNA), morpholino, or antisense oligonucleotide directed to a TE transcript; an inhibitor that blocks intercellular transmission of transposon genetic material or protein, or an inhibitor of post-translational processing or proteolysis of a transposon-encoded protein.

6. The method of claim 1, wherein the transposon is a retrotransposon.

7. The method of claim 6, wherein the retrotransposon is an LTR-retrotransposon.

8. The method of claim 6, wherein the retrotransposon is a non-LTR retrotransposon.

9. The method of claim 8, wherein the non-LTR retrotransposon is a LINE retrotransposon.

10. The method of claim 9, wherein the LINE retrotransposon is L1.

11. The method of claim 8, wherein the non-LTR retrotransposon is a SINE retrotransposon.

12. The method of claim 11, wherein the SINE retrotransposon is an Alu sequence.

13. The method of claim 1, wherein the transposon is a DNA transposon.

14. The method of claim 1, wherein the transposon is an autonomous element.

15. The method of claim 1, wherein the transposon is a nonautonomous element.

16. A method of treatment, comprising:
(a) administering to a subject having a TDP-43 associated neurodegenerative disorder a transposon inhibitor in an amount effective to reduce the expression level of a transposon;
(b) measuring the expression level of at least one transposon in a biological sample from the subject; and
(c) determining whether the measured transposon expression level in the subject exceeds a predetermined level, wherein the TDP-43 associated neurodegenerative disorder is frontotemporal lobar degeneration (FTLD).

17. The method of claim 16, wherein the transposon is an L1 LINE retrotransposon.

18. The method of claim 1, wherein the subject is a human.

19. The method of claim 16, wherein the subject is a human.

* * * * *

UNITED STATES PATENT AND TRADEMARK OFFICE
CERTIFICATE OF CORRECTION

PATENT NO. : 9,441,223 B2  
APPLICATION NO. : 14/019380  
DATED : September 13, 2016  
INVENTOR(S) : Josh Dubnau et al.

Page 1 of 1

It is certified that error appears in the above-identified patent and that said Letters Patent is hereby corrected as shown below:

At Column 1, Line 13, change "NIH 2 P30 CA45508-24 and NIH 5R01-NS067690" to -- CA045508 and NS067690 --.

Signed and Sealed this
Fifteenth Day of August, 2017

Joseph Matal
*Performing the Functions and Duties of the
Under Secretary of Commerce for Intellectual Property and
Director of the United States Patent and Trademark Office*